United States Patent

Li et al.

[11] Patent Number: 6,039,761
[45] Date of Patent: Mar. 21, 2000

[54] INTERVERTEBRAL SPACER AND TOOL AND METHOD FOR EMPLACEMENT THEREOF

[75] Inventors: Lehmann K. Li, Milford; Rhodemann Li, Greenwich, both of Conn.

[73] Assignee: Li Medical Technologies, Inc., Shelton, Conn.

[21] Appl. No.: 08/798,113

[22] Filed: Feb. 12, 1997

[51] Int. Cl.[7] .................................................. A61F 2/44
[52] U.S. Cl. ............................................................. 623/17
[58] Field of Search ......................... 623/17, 18; 606/60, 606/61

[56] References Cited

U.S. PATENT DOCUMENTS

| | | |
|---|---|---|
| 3,867,728 | 2/1975 | Stubstad et al. . |
| 3,875,595 | 4/1975 | Froning . |
| 4,309,777 | 1/1982 | Patil . |
| 4,349,921 | 9/1982 | Kuntz . |
| 4,743,256 | 5/1988 | Brantigan ................................. 623/17 |
| 4,772,287 | 9/1988 | Ray et al. ................................. 623/17 |
| 4,961,740 | 10/1990 | Ray et al. ................................. 606/61 |
| 5,015,247 | 5/1991 | Michelson ................................. 606/61 |
| 5,026,373 | 6/1991 | Ray et al. ................................. 606/61 |
| 5,055,104 | 10/1991 | Ray ........................................... 606/61 |
| 5,059,193 | 10/1991 | Kuslich ..................................... 606/61 |
| 5,071,437 | 12/1991 | Steffee ..................................... 623/17 |
| 5,123,926 | 6/1992 | Pisharodi ................................. 623/17 |
| 5,192,327 | 3/1993 | Brantigan ................................. 623/17 |
| 5,489,308 | 2/1996 | Kuslich et al. ........................... 623/17 |
| 5,522,899 | 6/1996 | Michelson ................................. 623/17 |
| 5,693,100 | 12/1997 | Pisharodi ................................. 623/17 |
| 5,716,416 | 2/1998 | Lin ........................................... 623/17 |

*Primary Examiner*—David J. Isabella
*Attorney, Agent, or Firm*—Pandiscio & Pandiscio

[57] ABSTRACT

An intervertebral spacer comprises a multiplicity of interconnected wall elements collapsible to a first configuration wherein the wall elements are disposed in a compact arrangement, and expandable to a second configuration wherein the wall elements are disposed in an expanded arrangement which is open at a generally planar top and a generally planar bottom thereof.

20 Claims, 19 Drawing Sheets

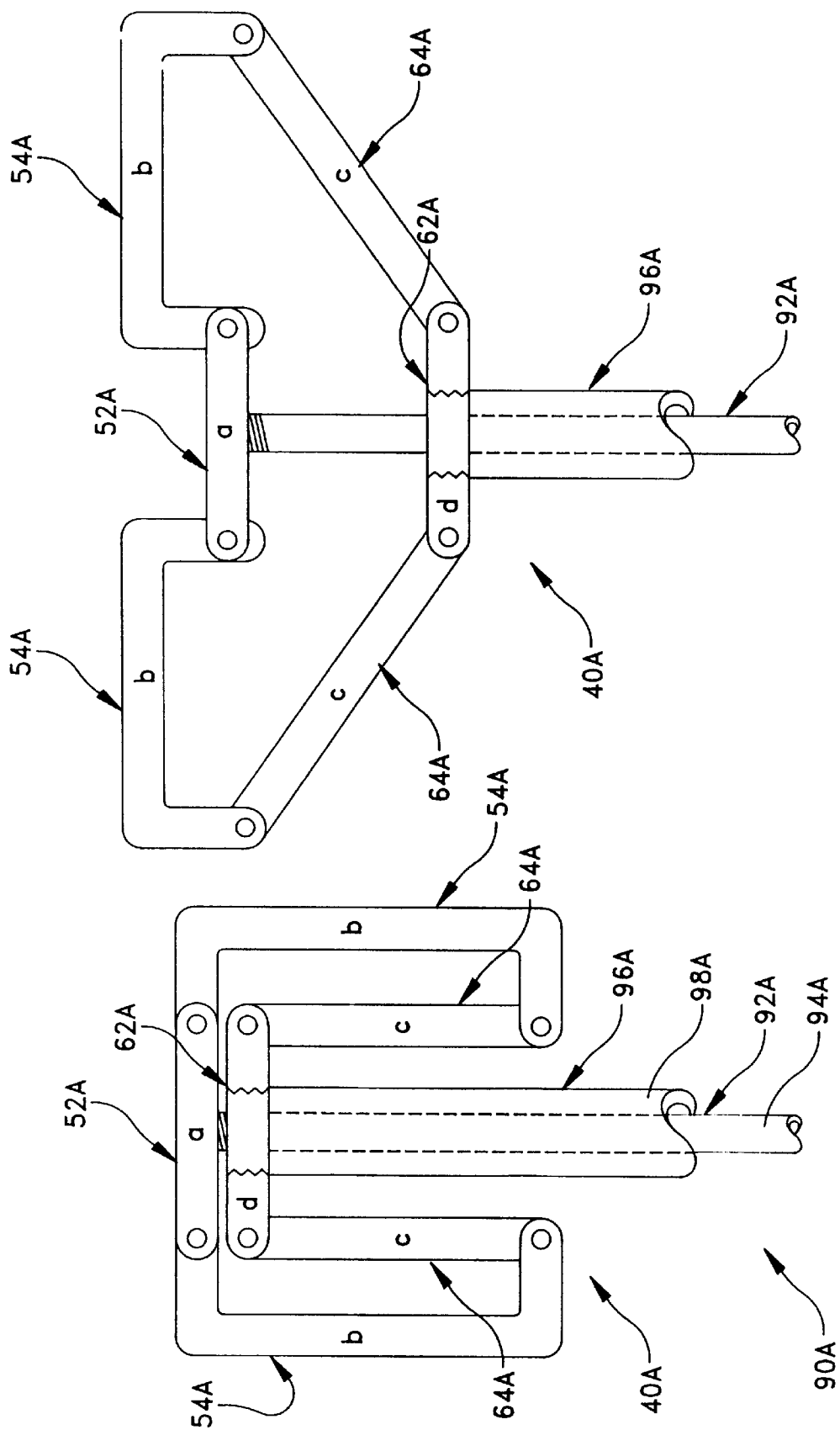

INTERVERTEBRAL SPACER AND TOOL AND METHOD FOR EMPLACEMENT THEREOF

FIELD OF THE INVENTION

This invention relates to surgical devices and procedures in general, and more particularly to an intervertebral spacer and a tool and a method for emplacement thereof between adjacent vertebrae.

BACKGROUND OF THE INVENTION

The human spine is a somewhat flexible structure including thirty-three vertebrae. The vertebrae are separated and cushioned from each other by fibro-cartilaginous structures referred to as intervertebral discs.

Artificial intervertebral discs, or intervertebral "spacers", are implanted in a disc space after the removal of a diseased or damaged natural intervertebral disc. Various types of artificial discs, or spacers, are described in U.S. Pat. No. 3,867,728, issued Feb. 25, 1975 to James A. Stubstad et al.; U.S. Pat. No. 3,875,595, issued Apr. 8, 1975 to Edward C. Froning; U.S. Pat. No. 4,309,777, issued Jan. 12, 1982 to Arun A. Patil; U.S. Pat. No. 4,349,921, issued Sep. 21, 1982 to J. David Kuntz; U.S. Pat. No. 4,743,256, issued May 10, 1988 to John W. Brantigan; U.S. Pat. No. 5,071,437, issued Dec. 10, 1991 to Arthur D. Steffee; U.S. Pat. No. 5,123,926, issued Jun. 23, 1992 to Madhavan Pisharodi; and U.S. Pat. No. 5,192,327, issued Mar. 9, 1993 to John W. Brantigan.

In another approach, the damaged disc is left in place and two capsules are implanted side by side, and spaced apart, in the damaged disc. The capsules are provided with (i) an outer layer of inert fibers intermingled with a bioresorbable material which attracts tissue in-growth, (ii) a bladder enveloped by the outer layer, and (iii) a thixotropic gel filling the bladder. See U.S. Pat. No. 4,772,287, issued Sep. 20, 1988 to Charles D. Ray.

In still another approach, similar in some respects to that described immediately above, fusion cages are placed side by side in a damaged disc between two normal natural vertebrae. These fusion cages comprise threaded members having holes therein. The natural vertebrae, in time, fuse with the cages. See U.S. Pat. No. 5,015,247, issued May 14, 1991 to Gary K. Michelson; U.S. Pat. No. 5,026,373, issued Jun. 25, 1991 to Charles D. Ray et al.; U.S. Pat. No. 5,489,308, issued Feb. 6, 1996 to Stephen D. Kuslich et al.; and U.S. Pat. No. 5,055,104, issued Oct. 8, 1991 to Charles D. Ray.

In U.S. Pat. No. 5,059,193, issued Oct. 22, 1991 to Stephen D. Kuslich, there is disclosed an expandable spinal implant for insertion into a bore formed between opposing vertebrae. This implant comprises a plurality of ribs deformable, in response to a deforming force, from a first shape to a second shape, with the ribs in the first shape being generally linear and the ribs in the second shape being arched outwardly in a ball-like configuration.

Despite such developments in the art, there remains a need for an effective intervertebral spacer and, in particular, a spacer which may be introduced into the patient's body through a relatively small incision.

OBJECTS OF THE INVENTION

Accordingly, one object of the present invention is to provide an improved intervertebral spacer which may be introduced into a patient's body in a collapsed and relatively small state and which, once in place, may be enlarged to occupy a larger space.

Another object of the present invention is to provide an inserter tool for deploying such an intervertebral spacer.

And another object of the present invention is to provide a method for emplacement of such an intervertebral spacer, utilizing a selected one of anterior, posterior, and oblique approaches.

Still another object of the present invention is to provide an improved intervertebral spacer which is adapted so as to provide a space between adjacent vertebrae for receiving selected materials, such as fusion-enhancing materials, therapeutic agents, artificial disc components, and the like.

SUMMARY OF THE INVENTION

These and other objects of the present invention are addressed by the provision and use of a novel intervertebral spacer comprising a multiplicity of interconnected wall elements collapsible to a first configuration wherein the wall elements are disposed in a compact arrangement, and expandable to a second configuration wherein the wall elements are disposed in an enlarged arrangement, the spacer in the enlarged arrangement being open at a generally planar top and a generally planar bottom thereof.

The objects of the present invention are further addressed by the provision and use of a novel intervertebral spacer comprising an endless series of wall elements collapsible to a first configuration wherein a portion of the wall elements are disposed internally of other of the wall elements so as to provide a compact body of the wall elements, and expandable to a second configuration wherein all of the wall elements are disposed at the periphery of an enlarged body of the wall elements.

The objects of the present invention are further addressed by the provision and use of a novel intervertebral spacer comprising a multiplicity of interconnected wall elements collapsible to a first configuration wherein the wall elements are disposed in a compact arrangement, and expandable to a second configuration wherein the wall elements are disposed in an enlarged arrangement, the spacer in the enlarged arrangement being open at a generally planar top and a generally planar bottom thereof, and the interconnected wall elements being pivotally connected together at a single end of each of the wall elements so as to be capable of assuming the aforementioned first configuration or the aforementioned second configuration. In one particular form of this embodiment of the invention, one or more of the wall elements may be formed so as to be flexible.

The objects of the present invention are further addressed by the provision and use of a novel intervertebral spacer comprising a top piece having a distal end and a proximal end, a bottom piece having a distal end and a proximal end, and a proximal plate interconnecting the top piece proximal end and the bottom piece proximal end and hingedly connected to at least one of the top piece and the bottom piece. The spacer further includes a distal plate hingedly connected at one edge thereof to one of the top piece distal end and the bottom piece distal end, the distal plate having a free edge opposite the one edge. At least one of the top piece and the bottom piece, and the distal plate, are movable to move the distal plate from a first position in which the distal plate one edge is generally coincident with the top and bottom piece distal ends and the distal plate extends toward the proximal plate and between the top and bottom pieces, to a second position in which the free edge of the distal plate is engaged in a groove in the other of the bottom piece and the top piece, and the distal plate is generally parallel to the proximal plate.

The objects of the present invention are further addressed by the provision and use of a novel intervertebral spacer and inserter tool assembly including a spacer comprising an endless series of wall elements collapsible to a first configuration wherein a portion of the wall elements are disposed internally of other of the wall elements so as to provide a compact body of the wall elements, and expandable to a second configuration wherein all of the wall elements are disposed at the periphery of an enlarged body of the wall elements. The wall elements include a distal connector wall element pivotally connected at each end thereof to an adjoining one of the wall elements and having a first connection structure thereon, the distal connector wall element and the adjoining wall elements together comprising at least a portion of the wall elements disposed internally of other of the wall elements when the spacer is in its aforementioned first configuration. The wall elements further include a proximal connector wall element pivotally connected at each end thereof to an adjacent one of the wall elements and having a second connection structure thereon, the proximal connector wall element and the adjacent wall elements together comprising at least a portion of the aforementioned other of the wall elements. The assembly still further includes an inserter tool comprising first and second portions. The inserter tool's first portion comprises a tube extending through the proximal connector wall element and releasably connected to the first connection structure of the distal connector wall element, whereby the tube can move the distal connector wall element and the adjoining ones of the wall elements from their internal disposition to their external disposition at the periphery of the enlarged body. The inserter tool's second portion comprises a tube releasably connected to the second connection structure of the proximal connector wall element, the tube of the inserter tool's first portion being axially movable in the tube of the inserter tool's second portion.

The objects of the present invention are still further addressed by the provision and use of a novel intervertebral spacer and inserter tool assembly including a spacer including a top piece having a distal end and a proximal end, a bottom piece having a distal end and a proximal end, and a proximal plate interconnecting the top piece proximal end and the bottom piece proximal end and hingedly connected to at least one of the top piece and the bottom piece. The proximal plate is provided with a central hole therethrough. The spacer further includes a distal plate hingedly connected at one edge thereof to one of the top piece distal end and the bottom piece distal end, the distal plate having a free edge opposite the one edge. At least one of the top piece and the bottom piece, and the distal plate, are movable to move the distal plate from a first position in which the distal plate one edge is generally coincident with the top and bottom piece distal ends, and the distal plate extends toward the proximal plate and between the top and bottom pieces, to a second position in which the free edge of the distal plate is engaged in a groove in the other of the bottom piece and the top piece, and the distal plate is generally parallel to the proximal plate. The assembly further includes an inserter tool comprising a tubular member connectable to the proximal plate and around the central hole, and a rod movable axially in the tube and through the central hole and having a distal end engageable with the spacer distal plate to move the distal plate from the first position to the second position.

The objects of the present invention are still further addressed by the provision and use of a method for emplacement of an intervertebral spacer, the method including the steps of: (i) providing an intervertebral spacer comprising a multiplicity of interconnected wall elements collapsible to a first configuration wherein the elements are disposed in a compact arrangement and expandable to a second configuration wherein the elements are disposed in an enlarged arrangement, the spacer in the enlarged arrangement being open at a generally planar top and a generally planar bottom thereof; (ii) inserting the spacer in the first configuration between two vertebrae; and (iii) applying a force to at least one of the wall elements to cause movement of the wall elements from the first configuration to the second configuration, with the open top of the spacer being adjacent a first of the vertebrae and the open bottom of the spacer being adjacent a second of the vertebrae. And in one particular form of the present invention, this method can also comprise the additional step of: (iv) inserting a selected material between at least two of the wall elements, wherein that material may be delivered from a source located outside the body to the site of the spacer using a tube, and further wherein that material might comprise fusion-enhancing materials, therapeutic agents, artificial disc components, and the like.

The objects of the present invention are still further addressed by the provision and use of a method for emplacement of an intervertebral spacer, the method including the steps of: (i) providing an intervertebral spacer comprising an endless series of wall elements collapsible to a first configuration wherein a portion of the wall elements is disposed internally of other of the wall elements so as to provide a compact body of the wall elements, and expandable to a second configuration wherein all of the wall elements are disposed at the periphery of an enlarged body of the wall elements; (ii) inserting the spacer in the first configuration between two vertebrae; and (iii) expanding the spacer to the second configuration. And in another particular form of the present invention, this method can also comprise the additional step of: (iv) inserting a selected material between at least two of the wall elements, wherein that material may be delivered from a source located outside the body to the site of the spacer using a tube, and further wherein that material might comprise fusion-enhancing materials, therapeutic agents, artificial disc components, and the like.

The objects of the present invention are still further addressed by the provision and use of a method for emplacement of an intervertebral spacer, wherein the method includes providing an intervertebral spacer comprising an endless series of wall elements collapsible to a first configuration so as to provide a compact body of the wall elements, and expandable to a second configuration wherein all of the wall elements are disposed at the periphery of an enlarged body of the wall elements. The method further includes providing an inserter tool having a first portion thereof for connection to a distal connector wall element of the wall elements, and a second portion thereof for connection to a proximal connector wall element of the wall elements, the inserter tool's first portion being axially movable in the inserter tool's second portion. The method still further includes the steps of: (i) connecting the inserter tool's second portion to the spacer's proximal connector wall element, and connecting the inserter tool's first portion to the spacer's distal connector wall element, and positioning the spacer in its collapsed configuration; (ii) extending the inserter tool and spacer through a patient's body toward a space between two adjacent vertebrae while the spacer is in its collapsed configuration; (iii) placing the spacer in the aforementioned space while the spacer is in its collapsed configuration; (iv) manipulating the inserter tool's first portion so as to move the spacer from its collapsed configuration to its expanded configuration; (v) disconnecting the inserter tool's first portion from the spacer; (vi) withdrawing the inserter tool's first portion from the spacer; (vii) disconnecting the inserter tool's second portion from the spacer; and (viii) withdrawing the inserter tool from the spacer and from the patient's body. And in another particular form of the present invention, this method can also include the step of: inserting a selected material between at least two of the wall elements, wherein that material may be delivered from a source located outside the body to the site of the spacer using a tube, and further wherein that material might comprise fusion-enhancing materials, therapeutic agents, artificial disc components, and the like. If desired, the spacer can be passed to the patient's spine by way of the patient's abdominal cavity.

The objects of the present invention are still further addressed by the provision and use of a method for emplacement of an intervertebral spacer, the method comprising the steps of providing an intervertebral spacer comprising a top piece having a distal end and a proximal end, and a bottom piece having a distal end and a proximal end. A proximal plate interconnects the top piece proximal end and the bottom piece proximal end and is hingedly connected to at least one of the top piece and the bottom piece. The proximal plate has a central hole therethrough. A distal plate is hingedly connected at one edge thereof to one of the top piece distal end and the bottom piece distal end, the distal plate having a free edge opposite the one edge. The at least one of the top piece and the bottom piece, and the distal plate, are movable to move the distal plate from a first position in which the distal plate one edge is generally coincident with the top and bottom piece distal ends, and the distal plate extends toward the proximal plate and between the top and bottom pieces, to a second position in which the free edge of the distal plate is engaged in a groove in the other of the bottom piece and the top piece and the distal plate is generally parallel to the proximal plate. The method further includes the steps of providing an inserter tool comprising a tubular member connectable to the proximal plate and around the central hole, and a rod movable axially in the tube and through the central hole, and having a distal end engageable with the spacer distal plate to move the distal plate from the first position to the second position. The method still further includes the steps of placing the spacer in a condition in which the distal plate is in the first position, connecting the tubular member to the spacer, directing a distal end of the spacer into a gap in a spinal column, driving the spacer into the gap, directing the rod through the tubular member and the proximal plate hole, and through the spacer, to engage the distal plate, driving the rod distally to cause the distal plate to move from the first position to the second position to expand the spacer, and withdrawing the rod and disconnecting the tubular member from the spacer, so as to leave the expanded spacer in the spinal column gap. The method can include the additional step of injecting a selected material into the expanded spacer.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 45 is a top plan view of still another alternative embodiment of spacer, shown in a collapsed state, and in combination with an inserter tool; and FIG. 46 is a view similar to FIG. 45, but showing the spacer fully expanded.

DETAILED DESCRIPTION OF THE PREFERRED EMBODIMENTS

Figure 1:
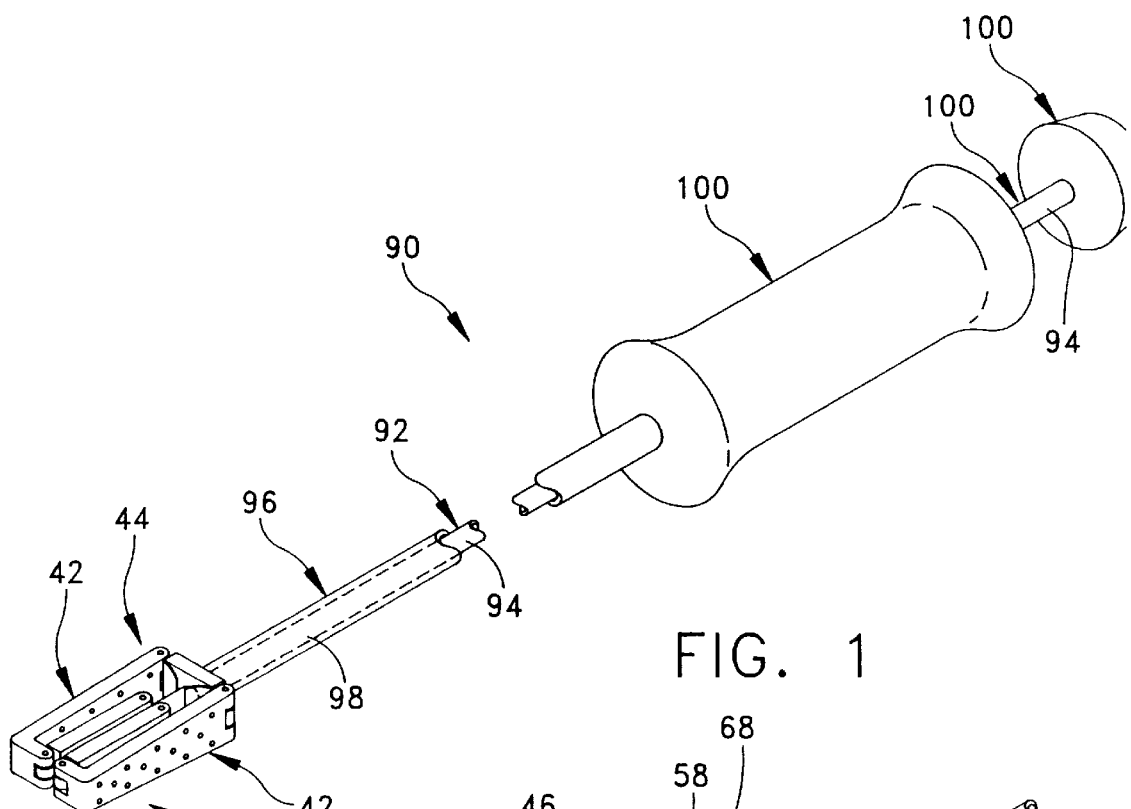
FIG. 1 is a perspective view of one form of intervertebral spacer illustrative of an embodiment of the invention, the spacer being shown in a collapsed state and connected to an inserter tool.
Figure 2:
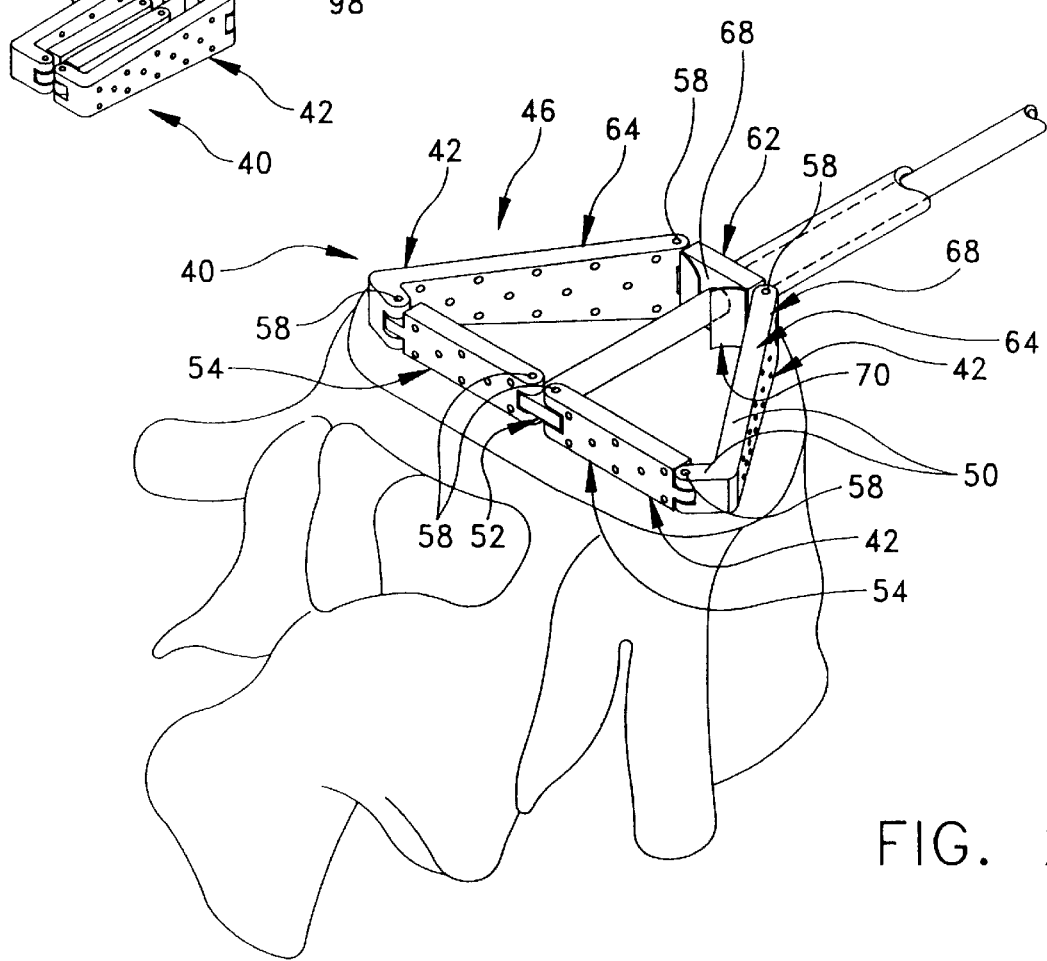
FIG. 2 is a perspective view of the spacer of FIG. 1 in position adjacent a vertebra and in an expanded state.

Referring first to FIGS. 1 and 2, it will be seen that an illustrative intervertebral spacer 40 includes an endless series of wall elements 42 collapsible to a first configuration 44 (FIG. 1) and expandable to a second configuration 46 (FIG. 2) so as to form an enlarged body of wall elements 42. An inserter tool 90 (FIG. 1) for spacer 40 includes a first portion 92 comprising an inner tube 94 connectable to one of the wall elements 42, and a second portion 96 comprising an outer tube 98. The inner tube 94 is slidably movable axially within outer tube 98 so as to effect expansion of spacer 40 from the first configuration 44. (FIG. 1) to the second configuration 46 (FIG. 2).

Figure 5:
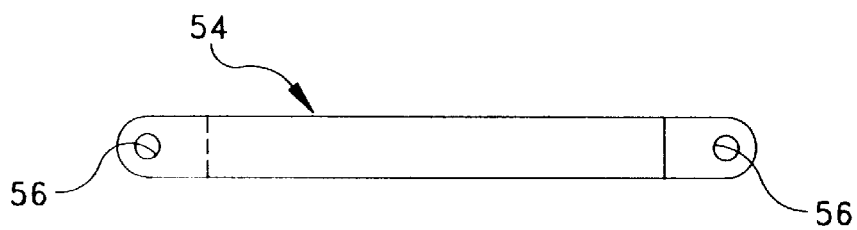
FIG. 5 is a top plan view of a distal wall element of the spacer of FIG. 2.
Figure 6:
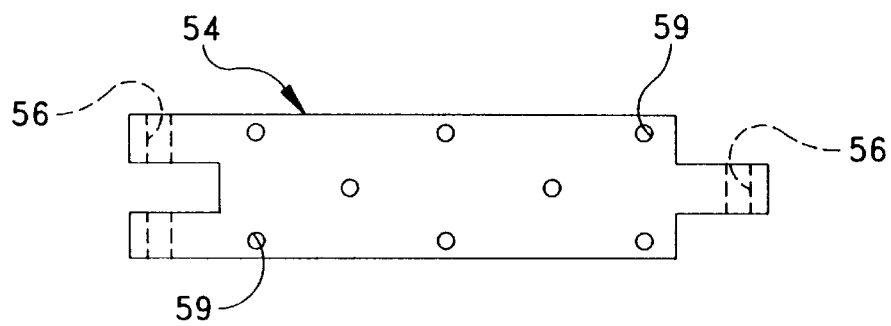
FIG. 6 is a side elevational view of the distal wall element of FIG. 5.
Figure 7:
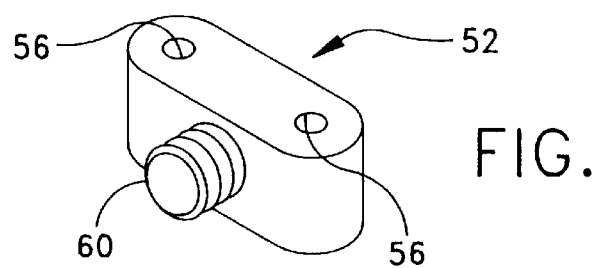
FIG. 7 is a perspective view of a distal connector wall element of the spacer of FIG. 2.
Figure 8:
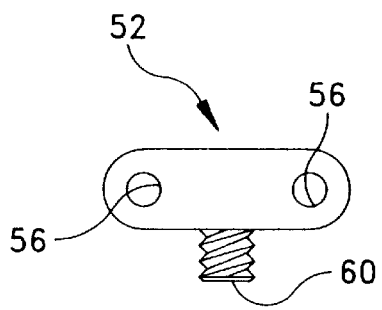
FIG. 8 is a top plan view of the distal connector wall element of FIG. 7.
Figure 9:
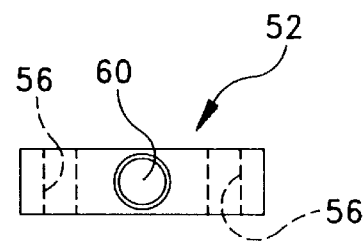
FIG. 9 is a front elevational view of the distal connector wall element of FIG. 7.
Figure 10:
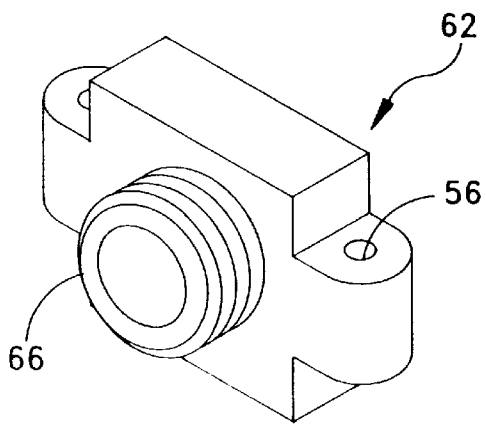
FIG. 10 is a perspective view of a proximal connector wall element of the spacer of FIG. 2.
Figure 11:
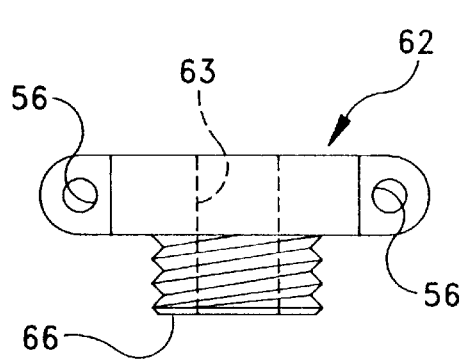
FIG. 11 is a top plan view of the proximal connector wall element of FIG. 10.
Figure 12:
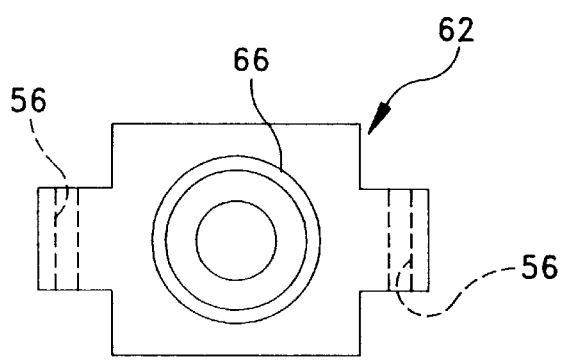
FIG. 12 is a front elevational view of the proximal connector wall element of FIG. 10.
Figure 13:
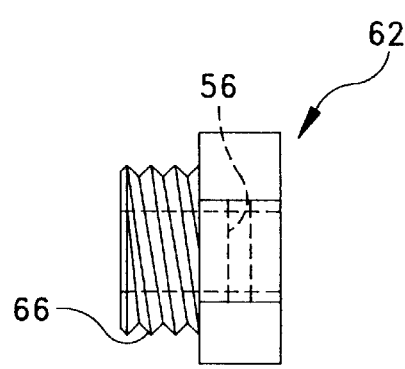
FIG. 13 is a side elevational view of the proximal connector wall element of FIG. 10.

The wall elements 42 preferably are elongated rigid rods 48, each in a preferred embodiment comprising only straight portions 50 and each being pivotally connected at both ends thereof to adjoining wall elements 42. The wall elements 42 include a distal connector wall element 52 (FIG. 2) pivotally connected at each end thereof to an adjoining one 54 of wall elements 42. Referring to FIGS. 7–9, it will be seen that the distal connector wall element 52 is provided with holes 56 for receiving pivot pins 58 (FIG. 2). Distal connector wall element 52 is also provided with a first connection structure 60 (FIGS. 7–9), preferably in the form of a threaded projection. Referring to FIGS. 5 and 6, it will be seen that the adjoining wall elements 54, which constitute distal wall elements, are also provided with holes 56 for receiving pivot pins 58, and may be provided with a multiplicity of small apertures 59. Apertures 59 are sized so as to permit blood to flow into and out of the region defined by the expanded spacer 40 (FIG. 2).

Figure 3:
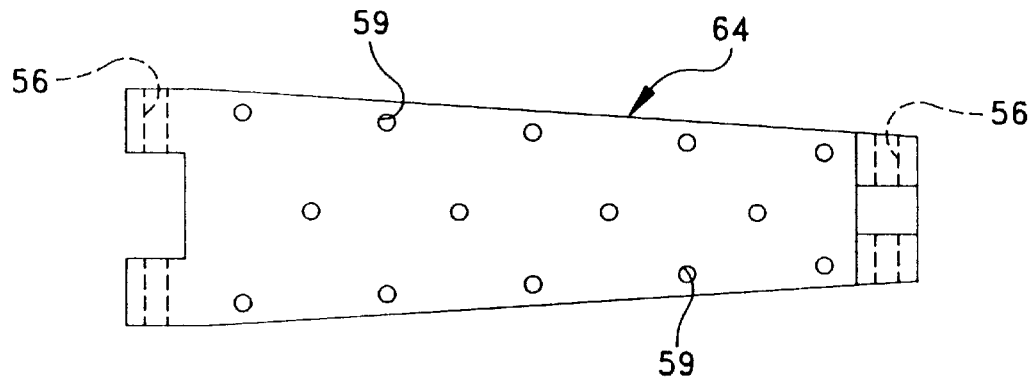
FIG. 3 is a side elevational view of a side wall element of the spacer of FIG. 2.
Figure 4:
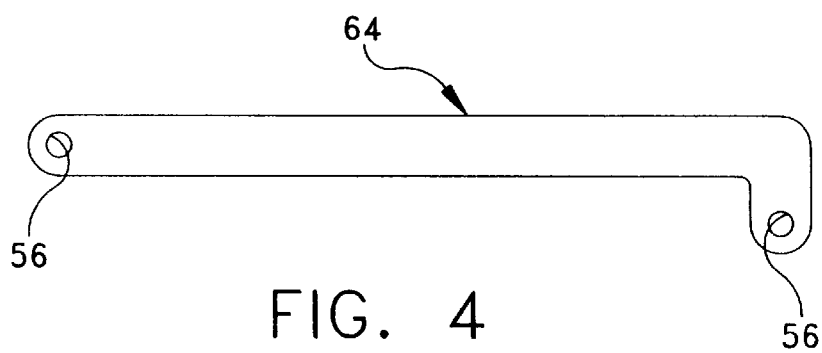
FIG. 4 is a top plan view of the side wall element of FIG. 3.

The wall elements 42 further include a proximal connector wall element 62 (FIG. 2) pivotally connected at each end thereof to an adjacent one 64 of the wall elements 42. Referring to FIGS. 10–13, it will be seen that the proximal connector wall element 62 is provided with holes 56 for receiving pivot pins 58 (FIG. 2). Proximal connector wall element 62 is also provided with a second connection structure 66, preferably in the form of a threaded hollow projection. A passageway 63 extends through proximal connector wall element 62 so as to communicate with the interior of the expanded spacer 40. Referring to FIGS. 3 and 4, it will be seen that the adjacent wall elements 64, which constitute side wall elements, are L-shaped and are provided with holes 56 for receiving pivot pins 58. The side elements 64 may also be provided with the small apertures 59 for permitting blood to flow into and out of the interior of the expanded spacer 40 (FIG. 2).

The side wall elements 64 may be somewhat wedge-shaped, as shown in FIGS. 1–3, or may be rectangularly-shaped, similar to wall elements 54 shown in FIG. 6.

As may be seen in FIG. 2, the side wall elements 64 are pivotally connected, each to one of the distal wall elements 54. Thus, the proximal connector wall element 62, side wall elements 64, distal wall elements 54, and distal connector wall element 52 form an endless series of wall elements. In the first configuration 44, shown in FIG. 1, a portion of the wall elements 42, specifically the distal connector wall element 52 and the two distal wall elements 54, are disposed internally of the other of the wall elements 42, specifically the L-shaped side elements 64 and the proximal connector wall element 62. The ability to place spacer 40 into this folded first configuration 44 (FIG. 1) allows the spacer to be easily introduced into the patient's body and then maneuvered to the surgical site, whereupon the spacer may be expanded to its working configuration 46 (FIG. 2).

Figure 16:
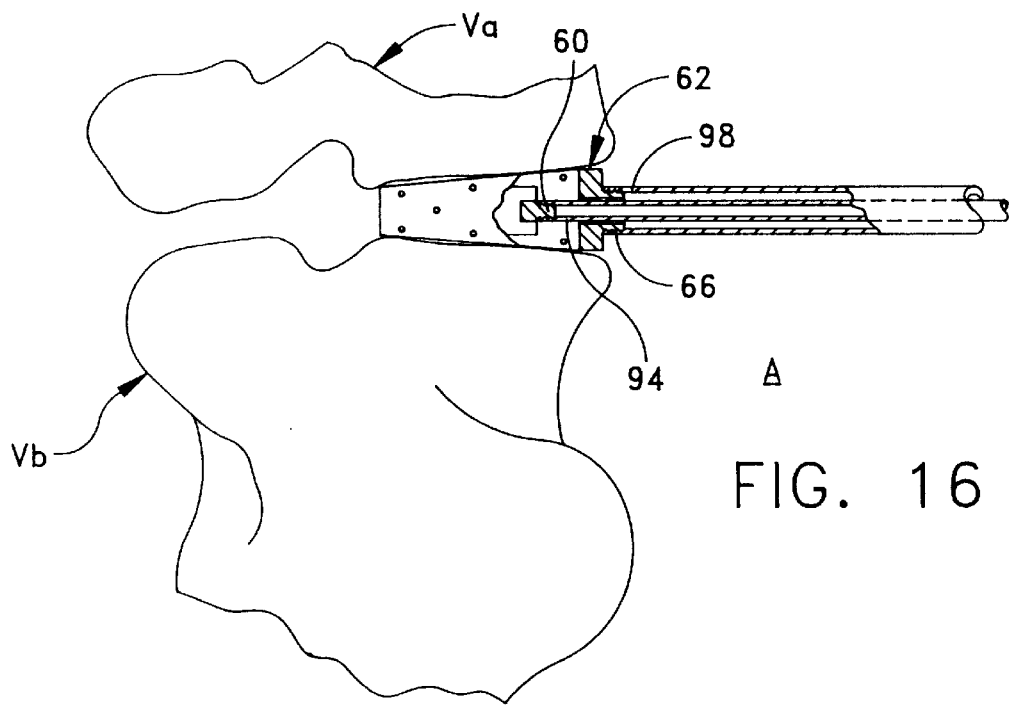
FIG. 16 is a side elevational view, partly in section, of the spacer of FIG. 1 being positioned in place between two vertebrae while the spacer is in its collapsed state.

Referring next to FIG. 16, it will be seen that inner tube 94 of inserter tool 90 is adapted for connection to the spacer's first connection structure 60. Similarly, outer tube 98 of inserter tool 90 is adapted for connection to the spacer's second connection structure 66, as by threaded engagement therewith. Thus, proximal connector wall element 62 may be held stationary by the inserter tool's outer tube 98, while distal connector wall element 52 may be moved about by the inserter tool's inner tube 94 so as to move spacer 40 between the first configuration 44 (FIG. 1) and the second configuration 46 (FIG. 2).

Figure 14:
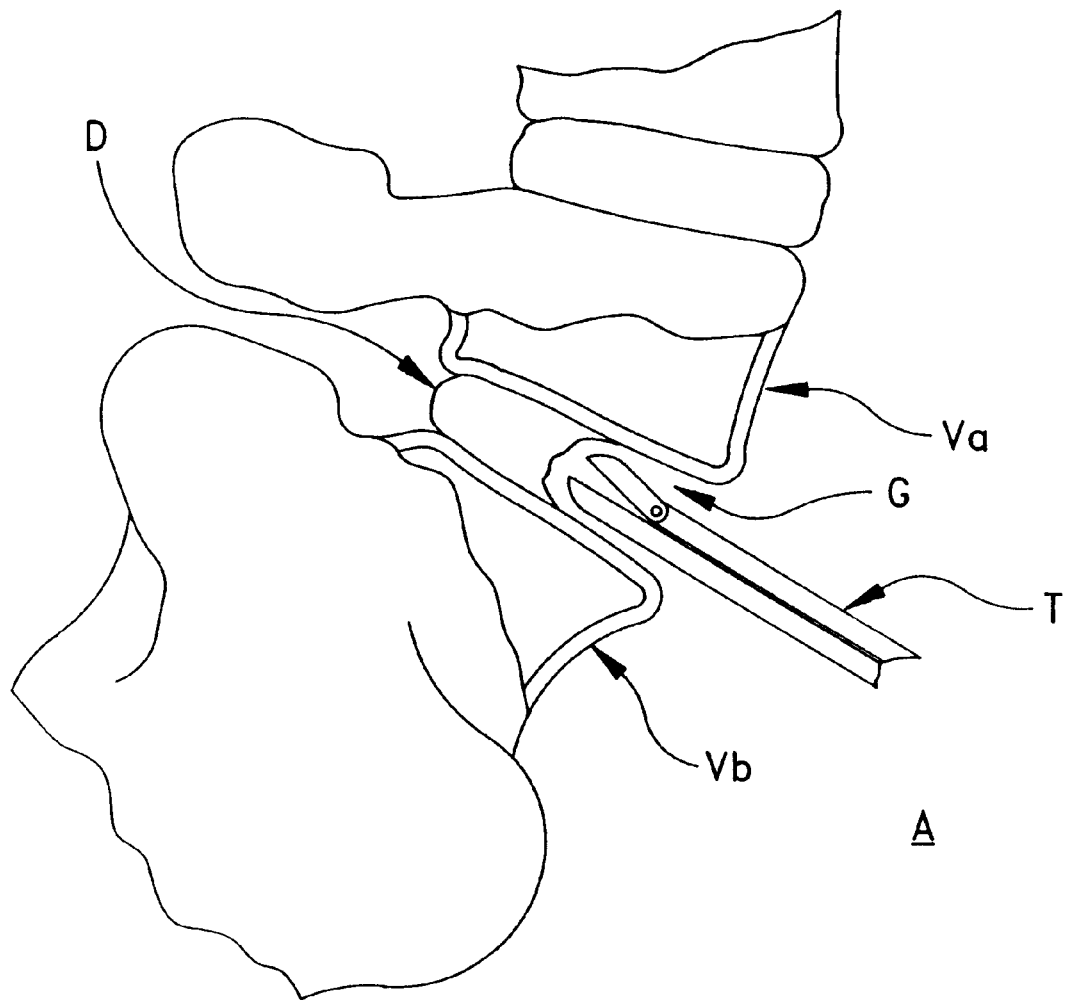
FIG. 14 is a diagrammatic side elevational view of a column of vertebrae, including a disc between a pair of adjacent vertebrae, and showing removal of a disc.

In a surgical operation, a diseased or damaged disc D (FIG. 14) is removed (wholly or in part) from between two vertebrae Va, Vb using a standard tool T of the sort well known in the art. Preferably tool T is inserted from the front, or abdominal, side of the body through a small incision (not shown) made in the front wall of the abdominal cavity A. Upon completion of removal (in whole or in part) of the afflicted disc D, there exists a space G between the vertebrae Va and Vb. Both during and after removal of the afflicted disc D, the space G may be maintained or widened by use of a conventional "jack" tool, not shown herein but well known in the art.

Figure 15:
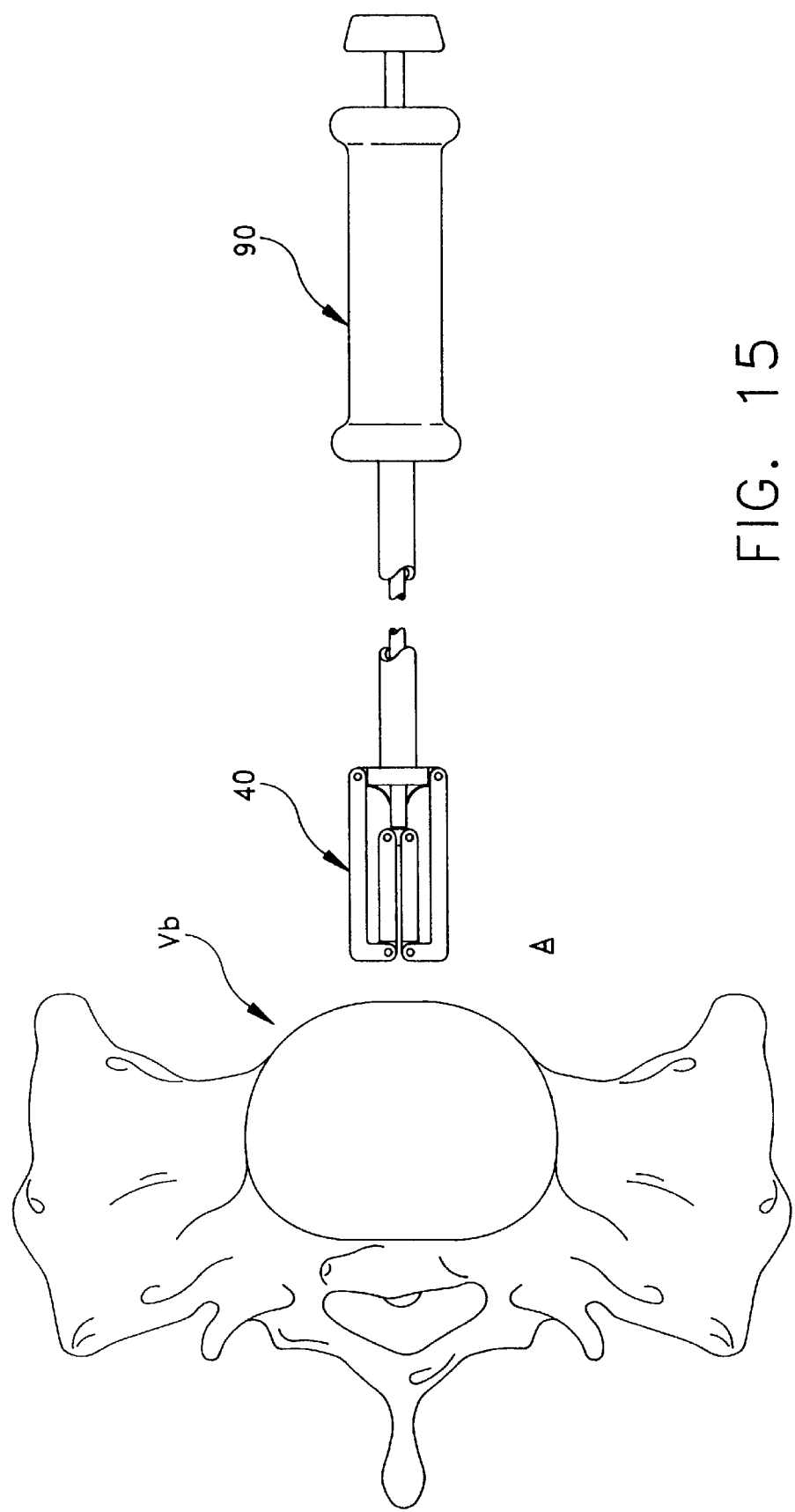
FIG. 15 is a top plan view of the spacer and insertion tool of FIG. 1 adjacent a vertebrae.

The tool 90, with spacer 40 attached thereto, is then extended through the previously made incision. The spacer 40 is inserted through the incision and carried toward the disc space G in its collapsed configuration 44 (FIG. 15). The spacer 40 is placed between the vertebrae Va, Vb, as shown in FIG. 16.

Figure 17:
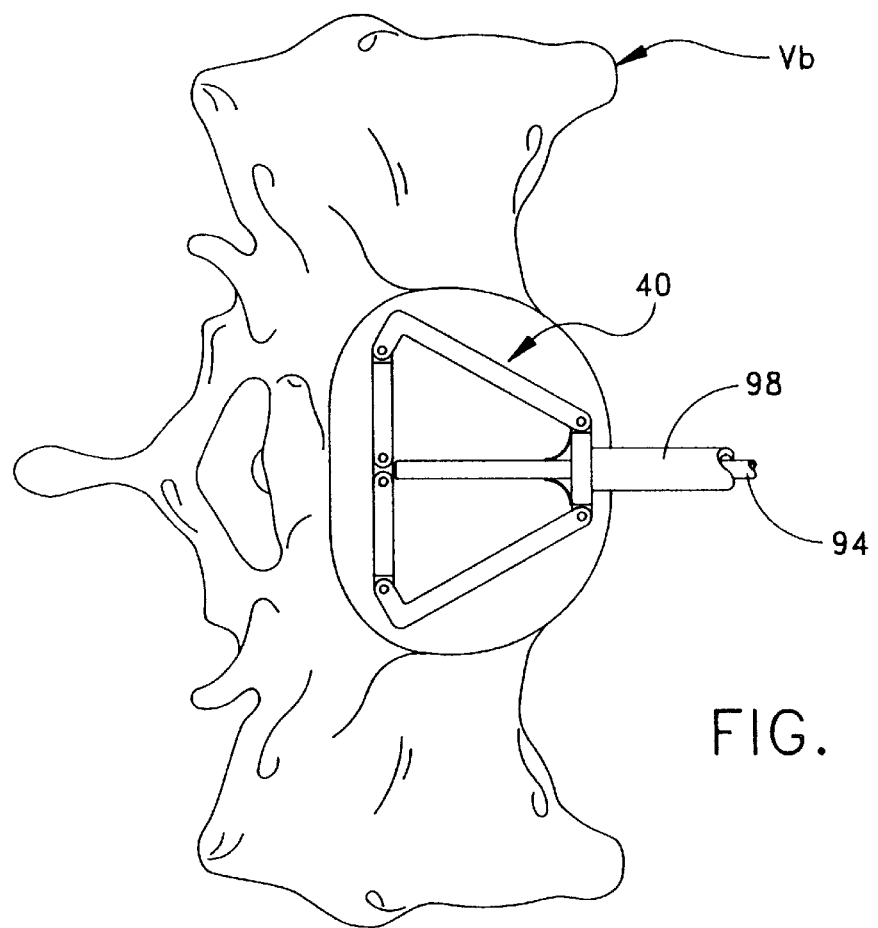
FIG. 17 is a top plan view of the spacer of FIG. 16, after the spacer has been moved into an expanded state.

The inserter tool's inner tube 94 is then moved distally, or leftwardly as viewed in FIGS. 16 and 17, so as to expand the spacer 40 to its enlarged configuration (FIG. 17). The tool 90 may be provided with a grip member 100 (FIG. 1) for holding outer tube 98 in place and a knob 102 for moving inner tube 94 within outer tube 98. After insertion and expansion of spacer 40, any "jack" tool present at the surgical site may be removed so as to allow vertebrae Va and Vb to close on the expanded spacer 40. Once in place, the wall elements 42 of spacer 40, which preferably are made of a suitable material to support the proper loading, e.g., an appropriate metal, plastic, ceramic or other material, maintain proper spacing between the vertebrae Va, Vb. Among the plastics found particularly suitable is an ultra high molecular weight polyethylene, which exhibits sufficient "springiness" to provide a shock absorption capability.

It will be appreciated that, once the spacer is in place, vertebrae Va and Vb will form "roofs" and "floors" for spacer 40, so as to define a substantially closed volumetric interior space. Of course, natural variations in the faces of vertebrae Va and Vb may result in some gaps existing between the upper and lower surfaces of spacer 40 and the opposing faces of vertebrae Va and Vb. However, for the purposes of the present invention, spacer 40, taken in conjunction with vertebrae Va and Vb, can be considered to define a substantially closed volumetric space. This is particularly true when one considers that this substantially closed volumetric space will preferably be filled with a fluid material having a gel-like consistency. Furthermore, it is to be appreciated that this closed volumetric space is a singular, uninterrupted region which communicates with substantially all of the two adjacent faces of the two adjacent vertebrae Va and Vb.

Figure 18:
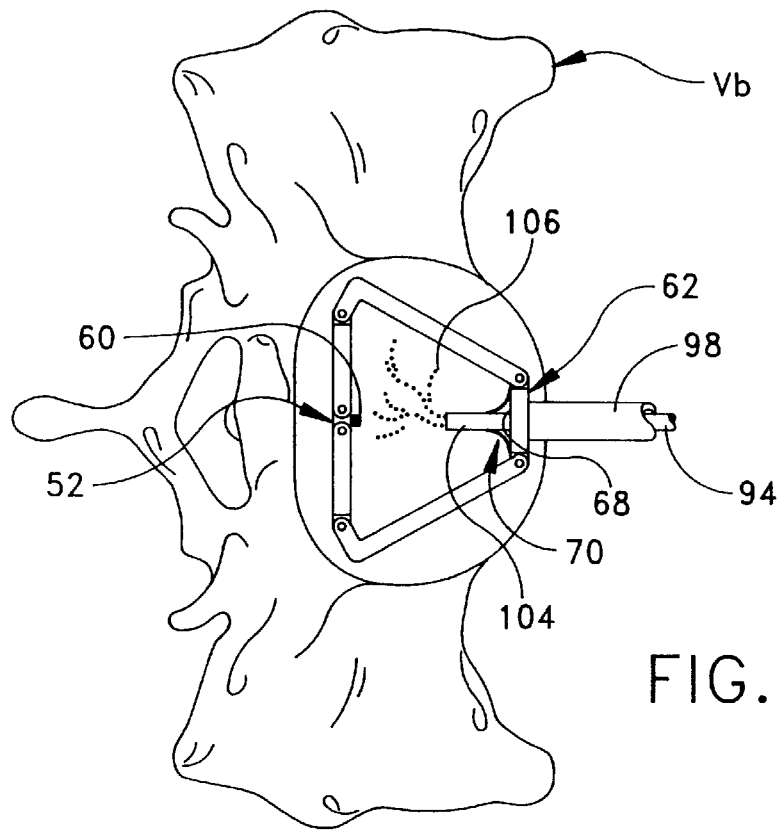
FIG. 18 is similar to FIG. 17, but shows part of the inserter tool retracted and filling the interior of the spacer with material.

Once spacer 40 is in place between the vertebrae Va, Vb and positioned in its expanded state, inner tube 94 is disconnected from first connection structure 60 of distal connector wall element 52. This may be done by turning knob 102 so that inner tube 94 is unscrewed from first connection structure 60 (FIG. 18). A distal end 104 of inner tube 94 is then moved rightwardly, as viewed in FIG. 18, to a position generally centrally of the spacer 40. The knob 102 (FIG. 1) is then removed from inner tube 94 and replaced by connection to a reservoir (not shown) of viscous fluid 106 (preferably of a gelatin-like bone chip composition, or artificial bone in the form of granules) and the fluid 106 is injected into the confines of spacer 40 (FIG. 18).

Figure 19:
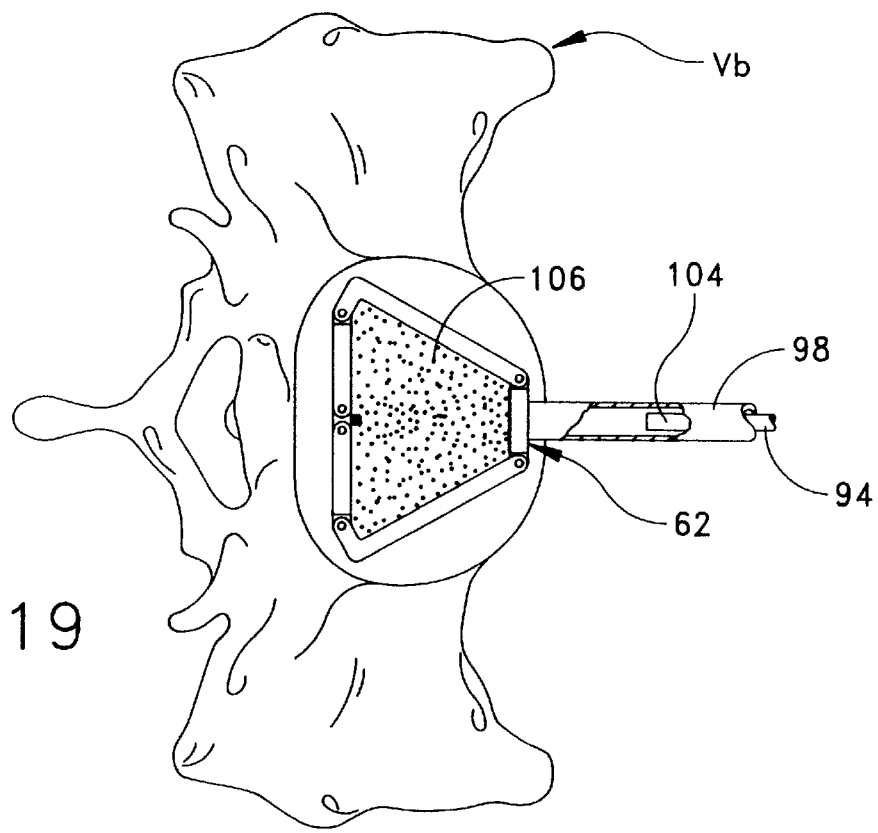
FIG. 19 is similar to FIG. 18, but shows the interior of the spacer filled with the injected material and the inserter tool in a further retracted position.

Referring to FIG. 19, it will be seen that spacer 40 is filled with the fluid material 106 and the inner tube 94 is then completely withdrawn from spacer 40.

In order to prevent viscous fluid 106 from leaking out through proximal connector wall element 62, the wall element 62 preferably is provided with one or more flap seal members 70 (FIGS. 2 and 18) which close against a distal surface 68 of the proximal connector wall element 62 as distal end 104 of inner tube 94 is withdrawn from spacer 40. This prevents fluid 106 from leaving the interior of spacer 40 through passageway 63. Furthermore, as seen in FIG. 2, the wall elements 42 are formed at their ends, and interconnected, so as to provide an endless upstanding wall, or dam, without substantial gaps therein. Thus, there are no substantial openings between wall elements 42 for the viscous fluid 106 to escape through. Also, the apertures 59 are of small enough diameter such that the viscous fluid 106 escapes only minimally, or not at all, through apertures 59. Of course, in this respect it should also be appreciated that fluid 106 preferably has a gel-like viscosity, such that relatively small openings between the elements of spacer 40, or between spacer 40 and vertebrae Va and Vb, will result in fairly modest leakage.

Figure 20:
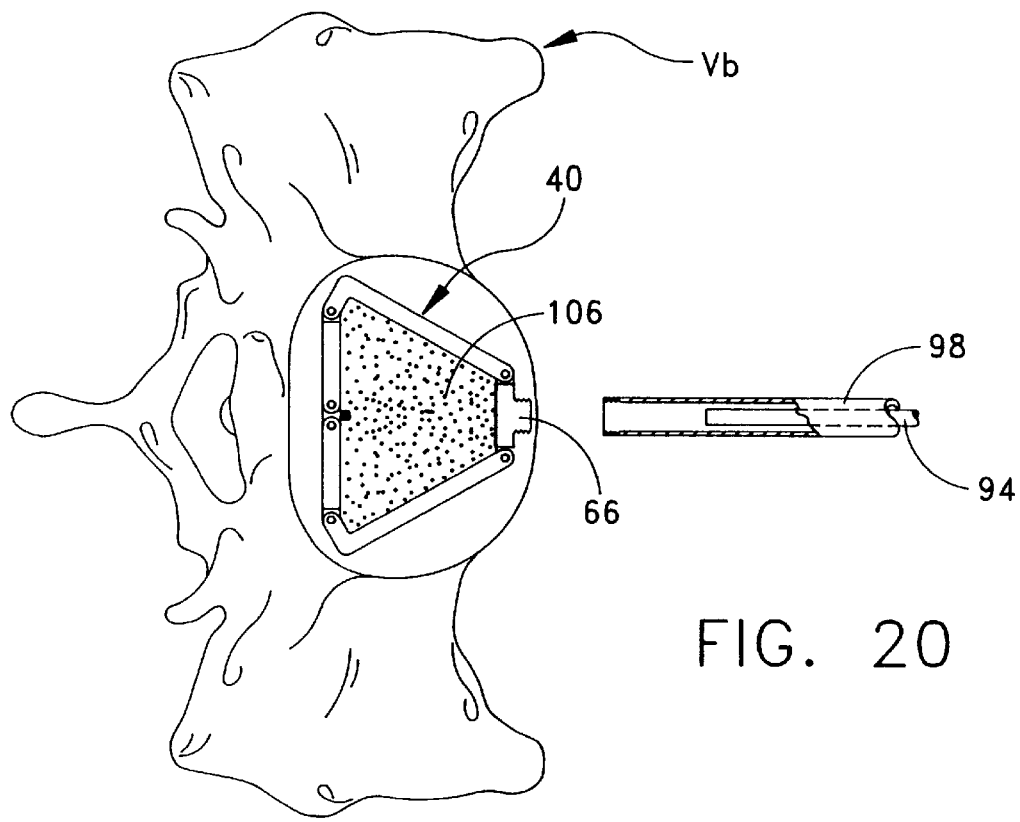
FIG. 20 is similar to FIG. 21, but shows the inserter tool disconnected from the spacer.
Figure 21:
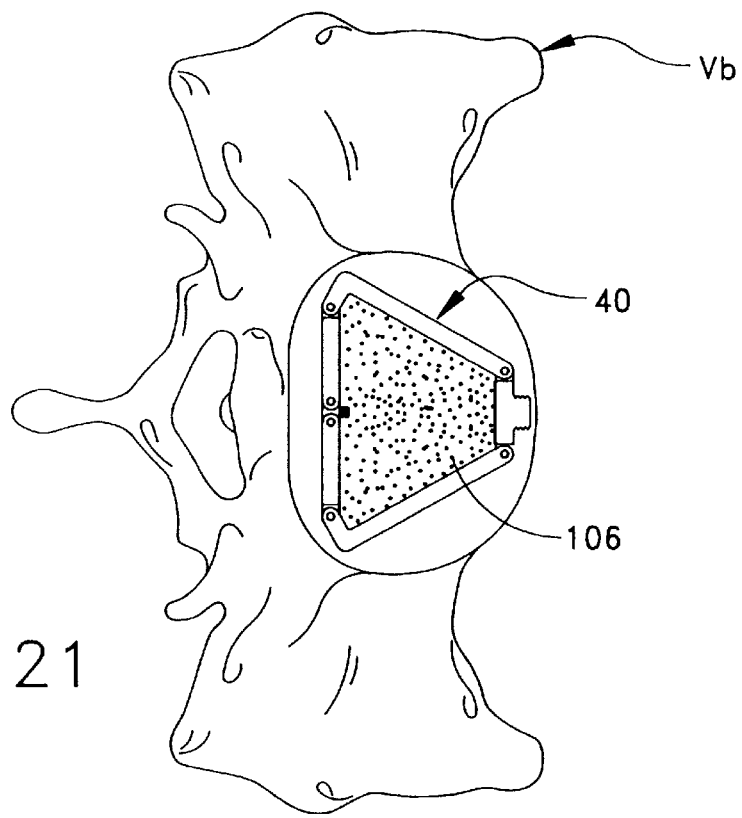
FIG. 21 is similar to FIG. 20, but with the inserter tool having been completely removed from the surgical site.

The inserter tool's outer tube 98 is then disconnected from the second connection structure 66 (FIG. 20), leaving spacer 40 in place (FIG. 21).

Vertebrae Va, Vb will thereafter fuse together on account of spacer 40 and the fluid 106 contained therein. In this respect it will be appreciated that, inasmuch as the adjacent vertebrae Va and Vb, respectively, form the "ceiling" and "floor" for spacer 40, fusion will occur over substantially the full extent of the disc faces, thus making such fusion extremely effective.

If desired, spacer 40 can be formed with apertures 59 larger than that shown. Furthermore, such apertures could have a configuration other than round. By way of example, spacer 40 could be formed with one or more large, rectangular apertures 59.

If desired, the upper and lower edges of the spacer's wall elements 42 may be roughened, or may be formed with ridges or other small projections, so as to help keep the spacer in position between vertebrae Va, Vb.

Figure 22:
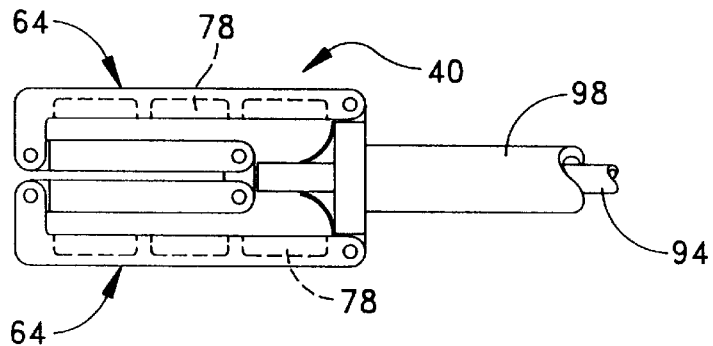
FIG. 22 is a top plan view of an alternative embodiment of spacer, shown in a collapsed state.
Figure 23:
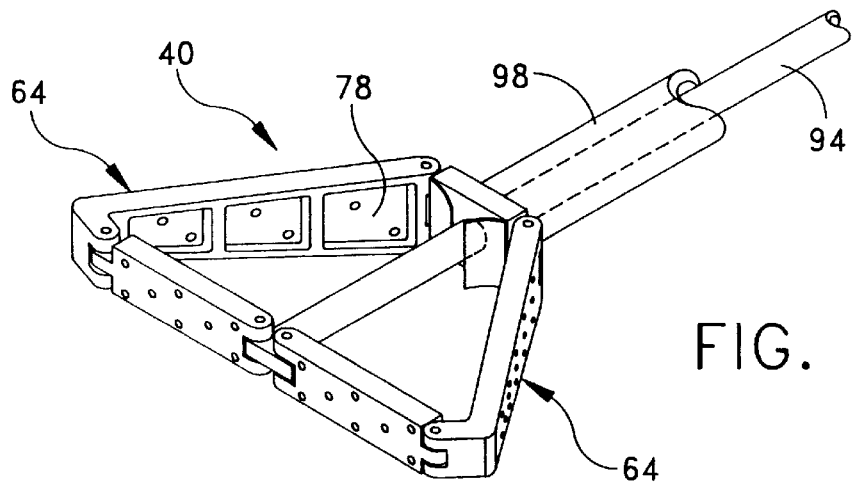
FIG. 23 is a perspective view of the spacer of FIG. 22, shown in an expanded state.
Figure 24:
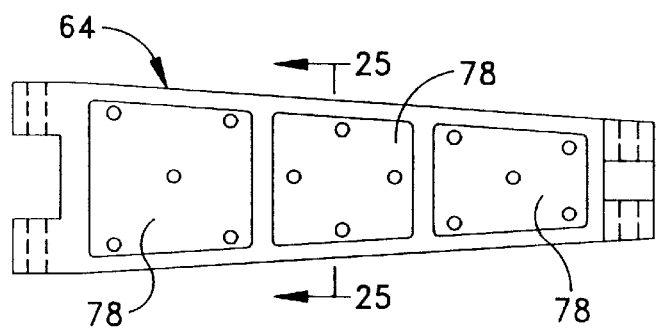
FIG. 24 is a side elevational view of a side wall element of the spacer of FIG. 23.
Figure 25:
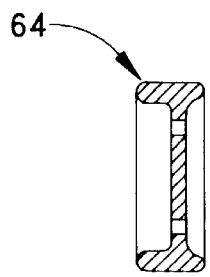
FIG. 25 is a sectional view taken along line 25—25 of FIG. 24.

In FIGS. 22 and 23, there is shown an alternative embodiment of spacer 40, essentially as described above, but in which side wall elements 64 (FIGS. 22–25) are provided with recesses 78 which reduce the weight of the side wall elements, while retaining rigidity and strength.

Figure 26:
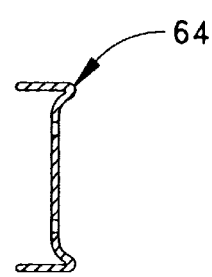
FIG. 26 is similar to FIG. 25, but illustrative of a further alternative embodiment of a side wall element of the spacer of FIG. 23.

In FIG. 26, there is shown another alternative embodiment in which the thickness of side element 64 is further reduced.

Figure 27:
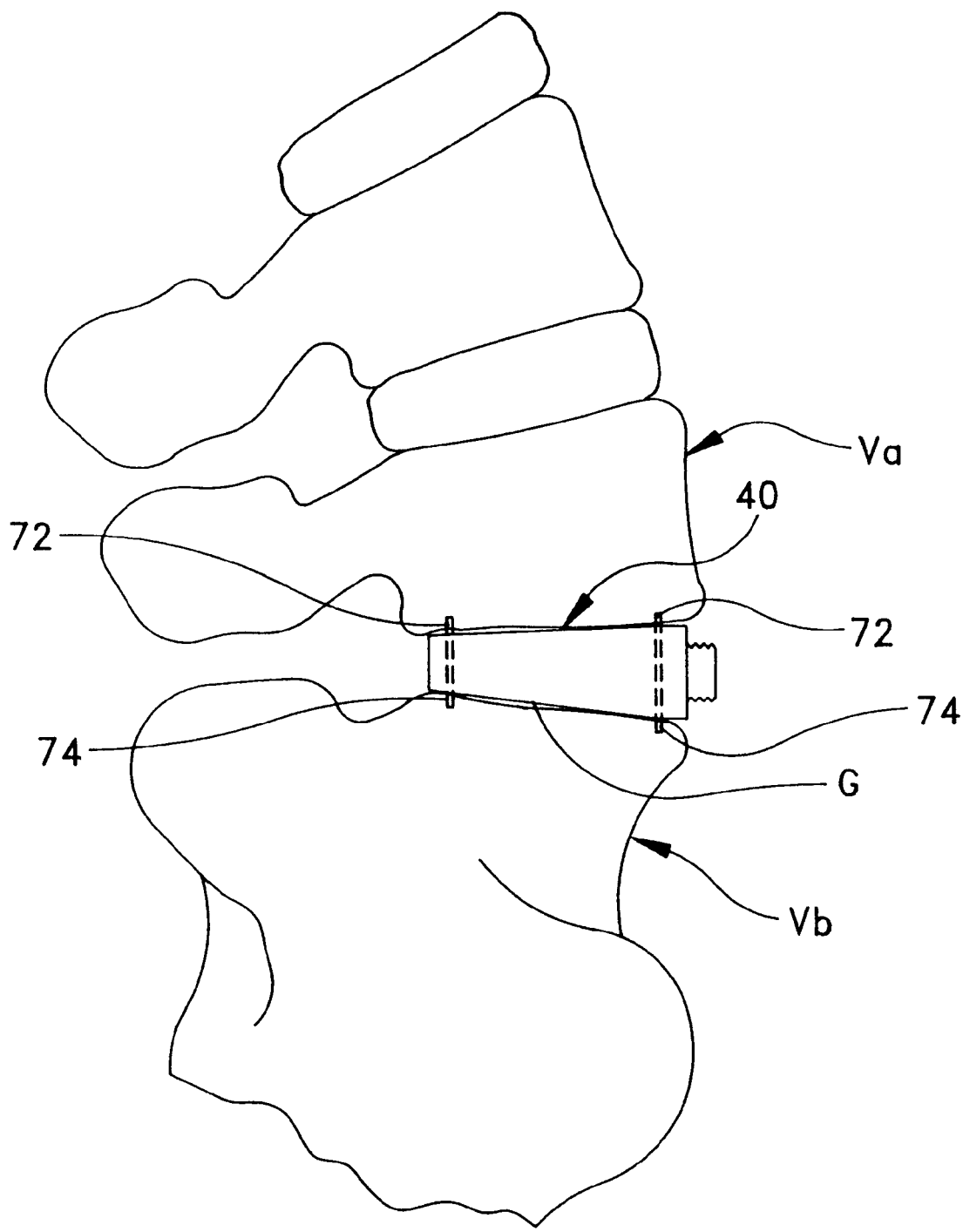
FIG. 27 is a diagrammatic side elevational view illustrative of another alternative embodiment of spacer, with the spacer being deployed in place between two vertebrae.

Referring next to FIG. 27, it will be seen that spacer 40 may be provided with pin portions 72, 74 extending upwardly and/or downwardly (both illustrated in FIG. 27) so as to enter into one or both of the vertebrae Va, Vb. In use of this embodiment, the aforementioned "jack" tool is used to enlarge disc space G sufficiently to permit insertion of spacer 40 therein. Upon removal of the jack, the upper vertebra Va settles down upon spacer 40, with the upper pin portions 72 setting into the vertebra Va. Similarly, the spacer 40 settles down upon vertebra Vb, with the lower pin portions 74 setting into vertebra Vb. The pin portions 72, 74 may be added to the previously described structure of spacer 40 or they may be formed from extensions of pivot pins 58.

Figure 28:
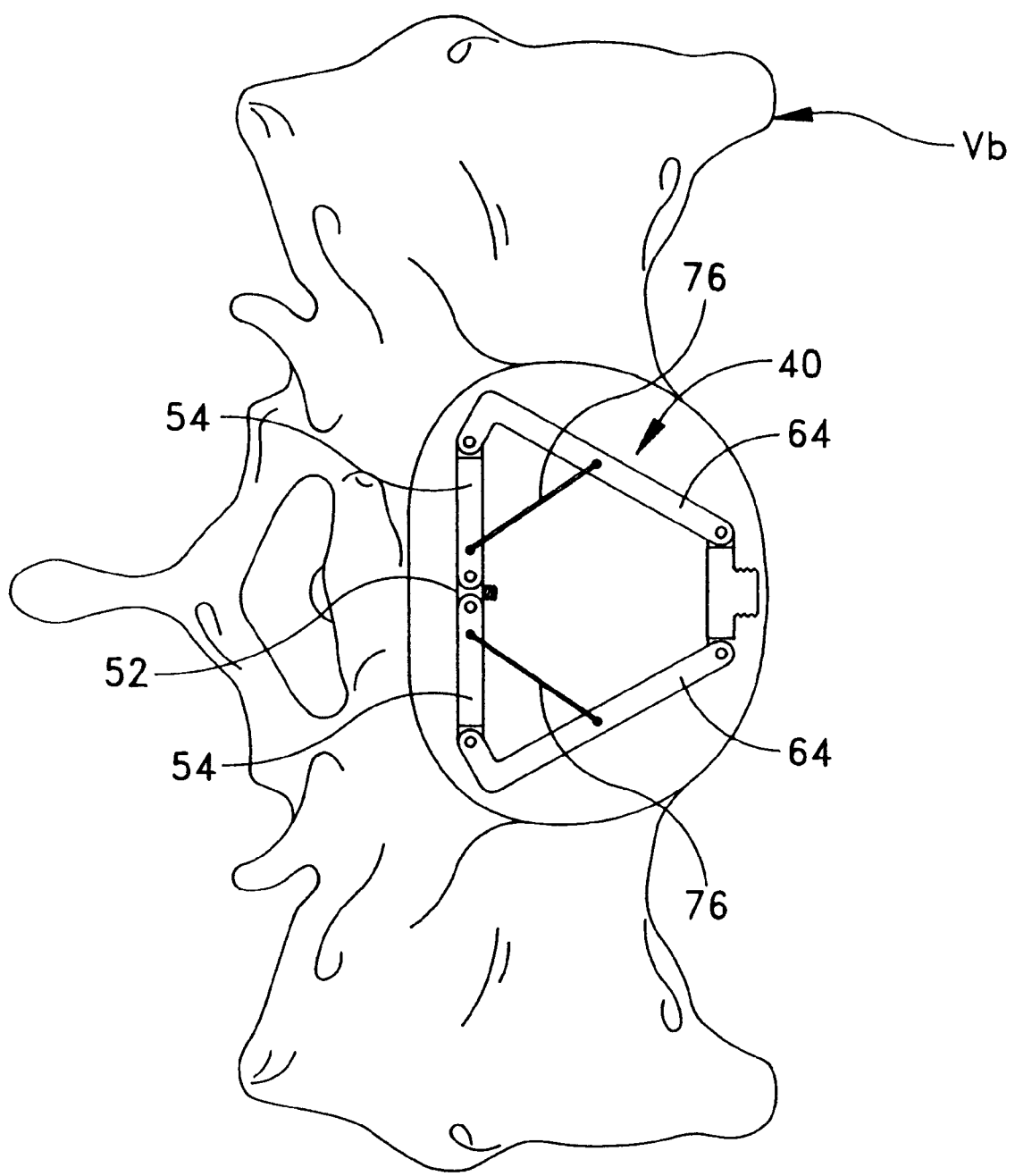
FIG. 28 is a top plan view of a further alternative embodiment of spacer.

As shown in FIG. 28, in order to prevent excessive distal (i.e., leftward in FIG. 28) movement of distal wall elements 54 when expanding spacer 40, wires 76, or the like, may be fixed on spacer 40, interconnecting each distal wall element 54 with a side wall element 64. The wires 76 are flexible so as to permit the wall elements 54, 64 to assume the collapsed configuration (FIG. 1) of spacer 40, but strong enough to prevent bowing distally of the distal wall elements 54 and distal connector wall element 52 during spacer deployment.

Figure 29:
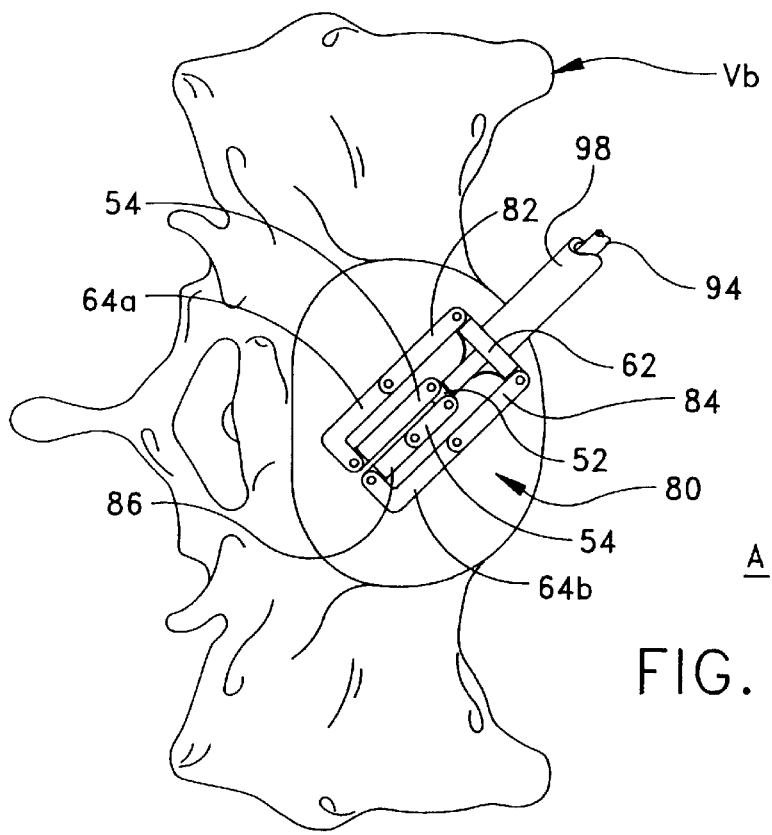
FIG. 29 is a top plan view of still another alternative embodiment of spacer, with the spacer being shown in a collapsed state and affixed to the inserter tool.
Figure 30:
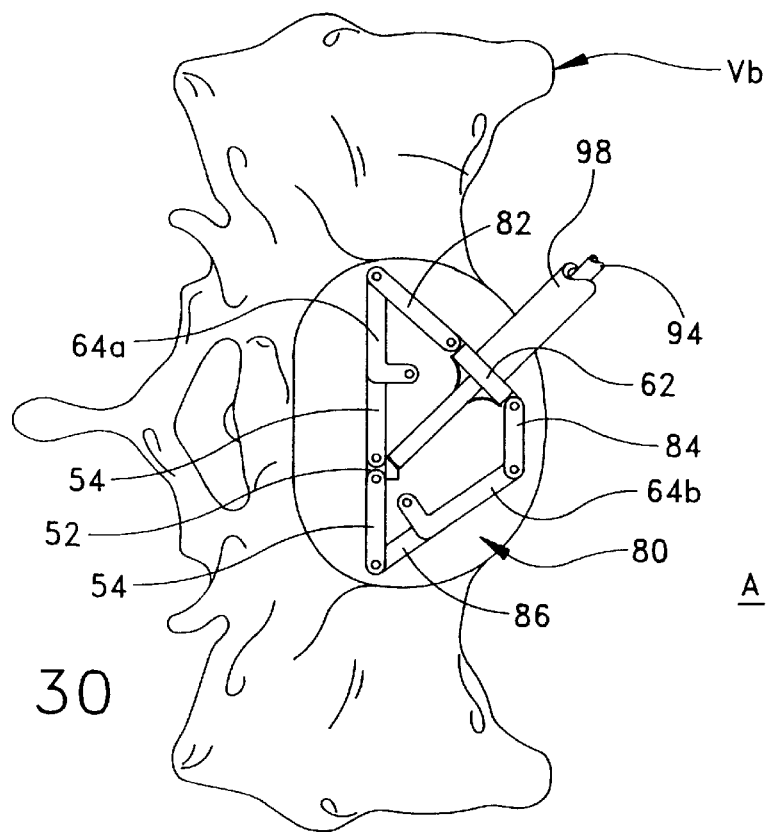
FIG. 30 is similar to FIG. 29, but illustrative of the spacer of FIG. 29 in an expanded state.

It is sometimes preferable to enter the abdominal cavity A obliquely, rather than straight on front-to-back. Referring next to FIGS. 29 and 30, it will be seen that for such occasions there is provided an alternative embodiment of spacer 80, substantially as described above, but having a modified arrangement of wall elements 42 to produce an asymmetrical expanded configuration (FIG. 30). In the illustrated embodiment, proximal wall elements 82, 84 each interconnect a proximal connector wall element 62 and an L-shaped wall element 64. As may be seen in FIG. 30, in this embodiment, in the expanded state, one of the L-shaped wall elements 64a becomes a distal wall element, generally in line with distal wall elements 54. A side wall element 86 interconnects the other L-shaped wall element 64b and one of the distal wall elements 54. Thus, though the approach through the abdominal cavity A is at an oblique angle, the spacer 80 is positioned on the vertebrae generally similarly to spacer 40.

In the foregoing embodiments, the spacer is provided with male screw mounts for engagement with counterpart female screw mounts on the inserter tool. Of course, this construction could be reversed, so that the spacer is provided with female screw mounts for engagement with male screw mounts on the inserter tool. Alternatively, other mechanical linkages of the sort well known in the art could also be used for attaching the spacer to the inserter tool.

Figure 31:
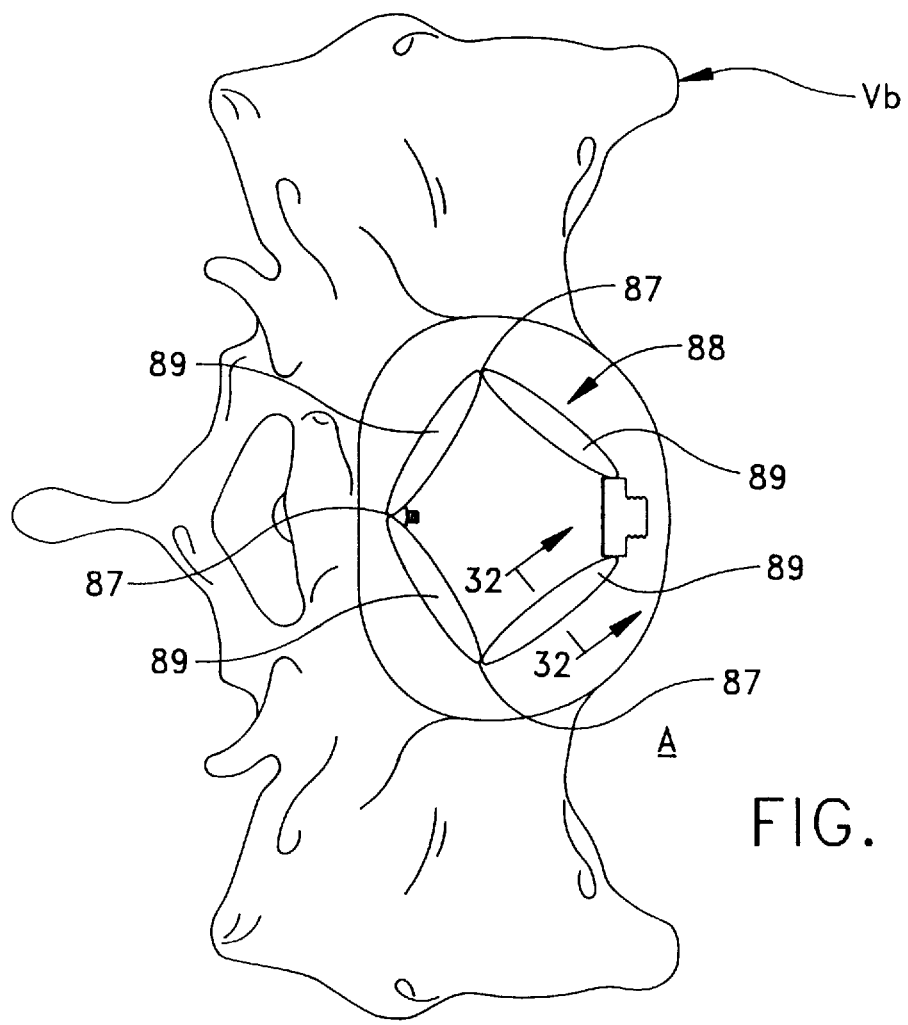
FIG. 31 is a top plan view of yet another alternative embodiment of spacer.
Figure 32:
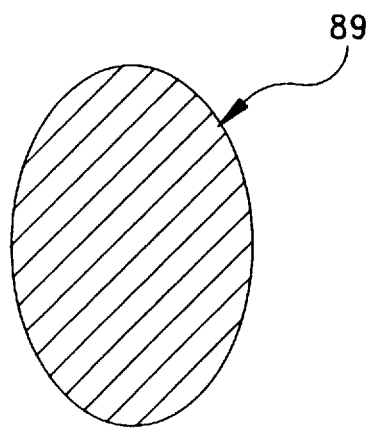
FIG. 32 is a sectional view taken along line 32—32 of FIG. 31.

In FIGS. 31 and 32, there is shown an alternative embodiment comprising a spacer 88 which functions in much the same manner as the spacer 40 of FIGS. 1 and 2, but in which wall elements 89 are each elongated bodies of elastomer material interconnected by living hinges 87, and which are collapsible to a first configuration similar to that shown in FIG. 1, and expandable to a second configuration, as shown in FIG. 31. The spacer 88 is emplaced in the same manner as is spacer 40, and may be modified in a manner similar to the spacer 80 of FIG. 30 so as to provide an asymmetrical expanded configuration.

In the foregoing embodiments, the inserter tool's inner tube 94 is intended to be used to insert fluid material 106 into the interior of the spacer. However, it should also be appreciated that the inserter tool's outer tube 98 could also be used for this purpose, after inner tube 94 is withdrawn from the spacer and from outer tube 98.

Figure 33:
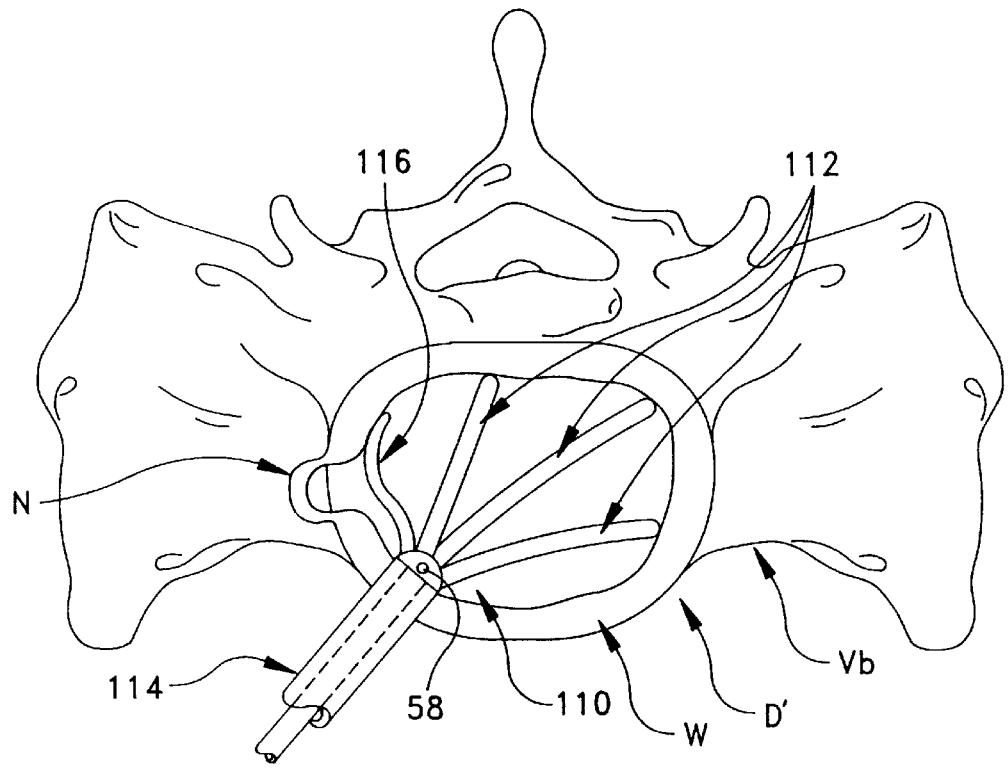
FIG. 33 is a top plain view of still another alternative embodiment of spacer.

In FIG. 33, there is shown another alternative embodiment of the invention. In this construction, a spacer 110 is provided which can be used in conjunction with a herniated natural disc D' which has been "hollowed out" so as to leave standing a rounded disc wall W. In this embodiment, the spacer 110 includes a plurality of wall elements 112 which are pivotally anchored at one end and movable through an inserter tube 114 into the enclosed area of the natural disc D'. The wall elements 112, upon emergence from the tube 114, tend to spread by virtue of a leaf-spring-like self-bias in the wall elements 112. The wall elements 112 provide support between the vertebrae Va and Vb which are disposed above and below the herniated disc D'.

The spacer 110 further includes a flexible wall element 116 which is biased to spring outboard toward the exterior of the natural disc wall W so as to close off the flow of interior disk matter to a herniated nucleus pulposus N which may be impinging on a spinal nerve (not shown).

Once the spacer 110 is in place, the tube 114 may be disconnected from the spacer 110 and used to inject the material 106 into the area bounded by wall W and flexible element 116. Thereafter, tube 114 is withdrawn.

Figure 34:
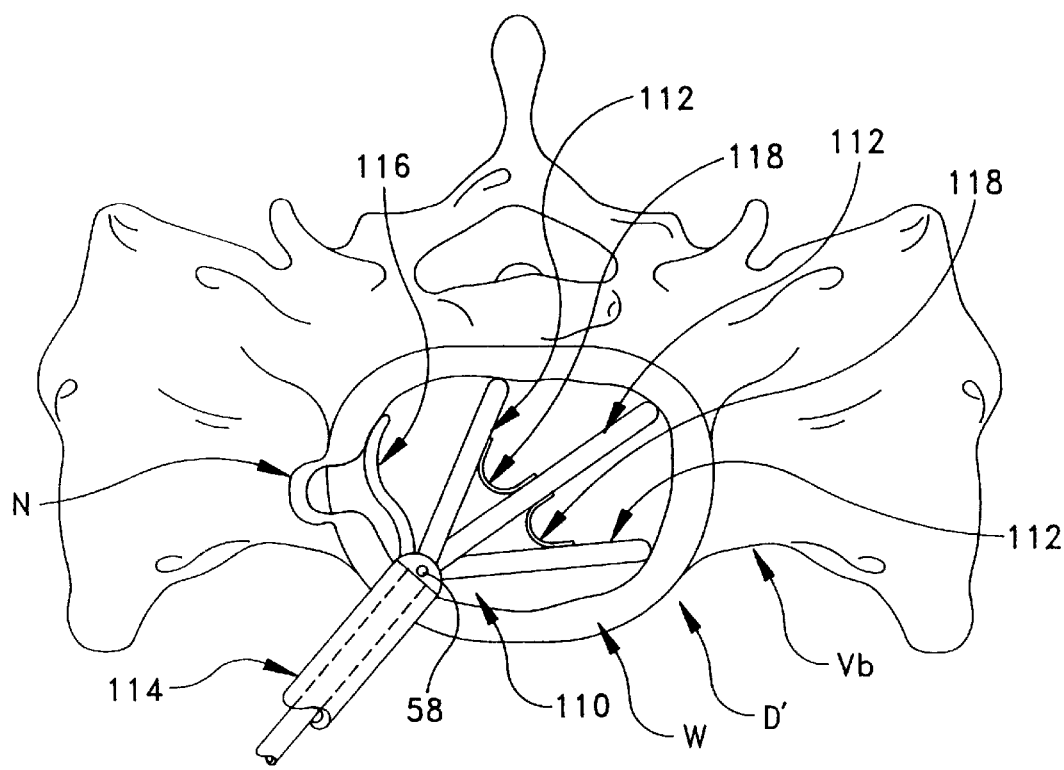
FIG. 34 is similar to FIG. 33, but showing a variation of the spacer of FIG. 33.

As shown in FIG. 34, the wall elements 112 alternatively may be rigid elements urged into their expanded position within the wall W by leaf springs 118 which are positioned therebetween.

The material 106 may be a bone chip composition, as noted above, or it may be a bone graft medium which is capable of growing into both the upper and lower adjacent vertebrae Va, Vb. Such growth causes the spacer to fuse to the adjacent vertebrae so as to lock the two vertebrae together. Similarly, the material 106 can comprise a biocompatible bonding medium so as to lock the two vertebrae Va, Vb together.

Figure 35:
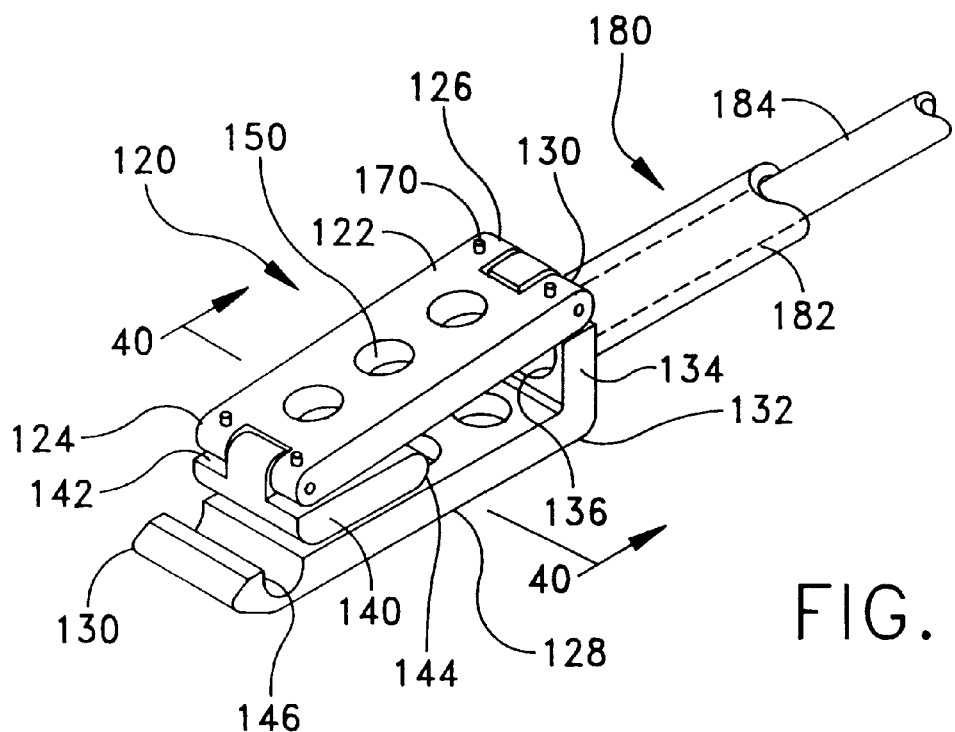
FIG. 35 is a perspective view illustrative of a still further alternative embodiment of spacer, shown in a collapsed state, and in combination with an inserter tool.

Referring next to FIG. 35, it will be seen that in an alternative embodiment a spacer 120 includes a top piece 122 having a distal end 124 and a proximal end 126, and a bottom piece 128 having a distal end 130 and a proximal end 132. A proximal plate 134 interconnects top piece proximal end 126 and bottom piece proximal end 132. Proximal plate 134 is hingedly connected to at least one of the top piece 122 and bottom piece 128. In FIGS. 35–39, proximal plate 134 is shown hingedly connected to top piece 122. The opposite, non-hinged edge of proximal plate 134 may be fixed to bottom piece proximal end 132, or may be integral therewith. The proximal plate 134 upstands from bottom piece 128 normal to bottom piece 128 or obtusely transverse to bottom piece 128 to provide a fixed spread between top piece proximal end 126 and bottom piece proximal end 132. Proximal plate 134 is provided with a central hole 136, to be discussed further hereinbelow.

Figure 36:
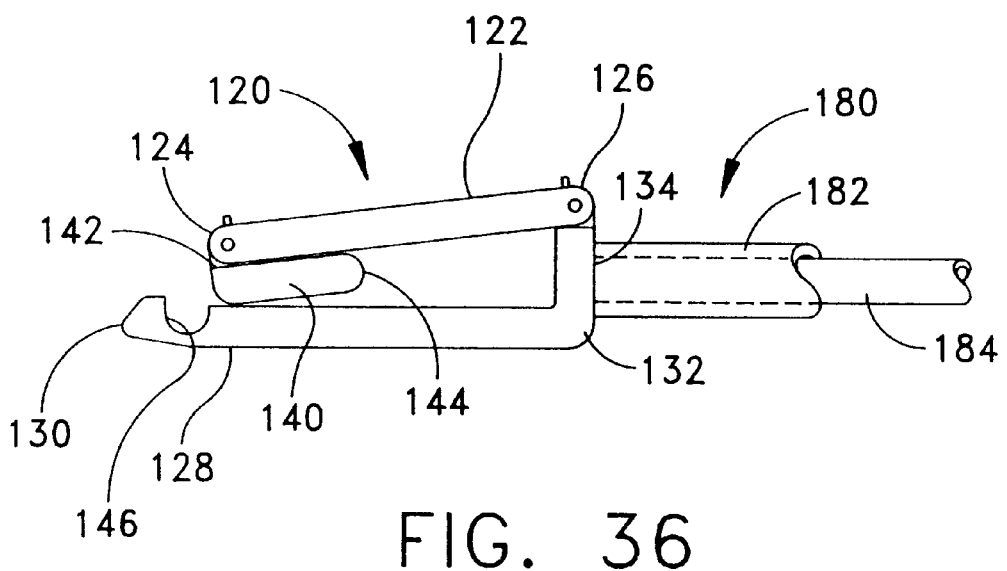
FIG. 36 is a side elevational view of the spacer of FIG. 35.
Figure 37:
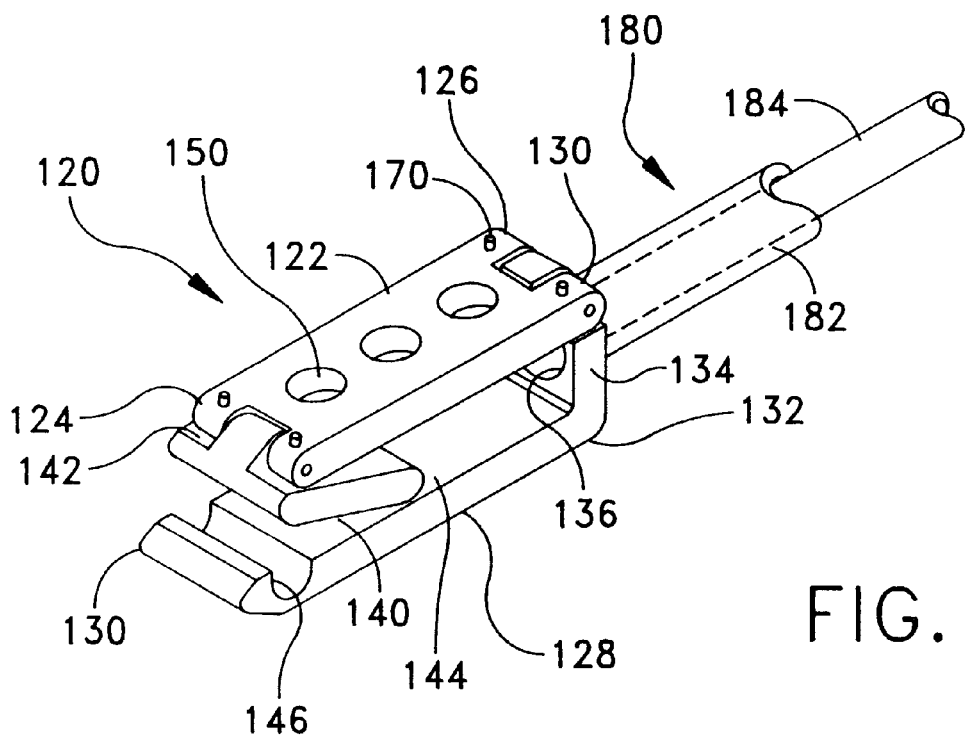
FIG. 37 is similar to FIG. 35, but showing the spacer being expanded.
Figure 38:
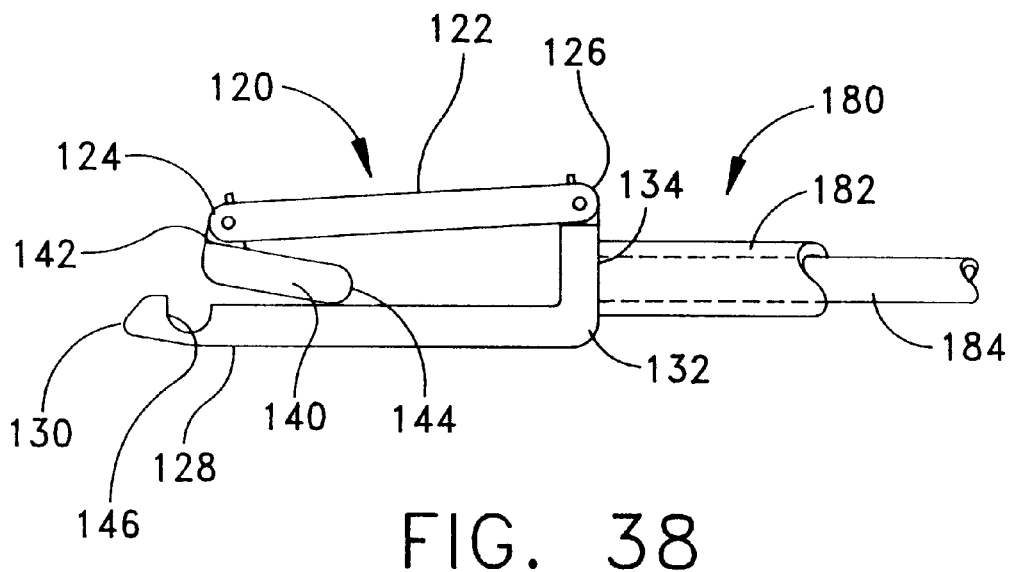
FIG. 38 is a side elevational view of the spacer of FIG. 37.
Figure 39:
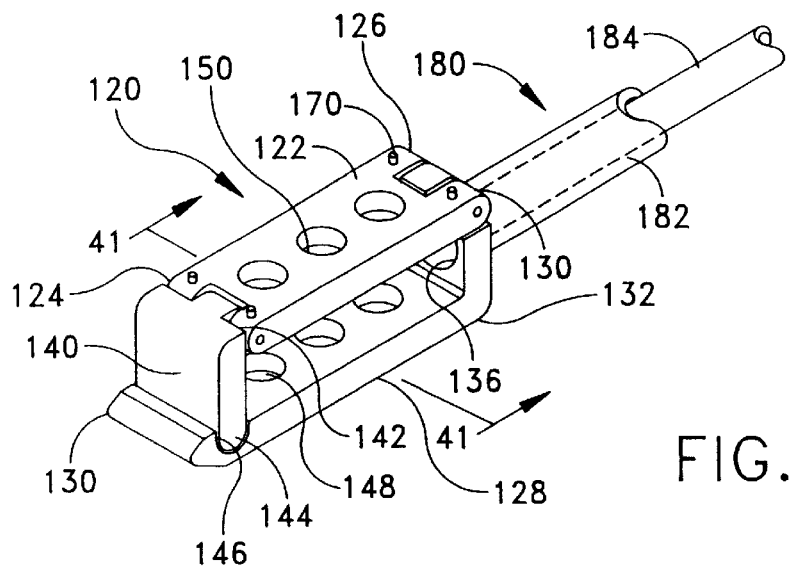
FIG. 39 is similar to FIG. 37, but showing the spacer fully expanded.

A distal plate 140 is hingedly connected at one edge 142 thereof to one of the top piece distal end 124 and bottom piece distal end 130, the former being illustrated in FIGS. 35–39. Distal plate 140 is provided with a free edge 144 opposite from the one edge 142. Bottom piece 128 is provided with a groove 146 configured to receive the free edge 144 of distal plate 140. As shown in FIGS. 37–39, distal plate 140 is movable from a first position (FIG. 35) in which distal plate edge 142 is generally coincident with top piece distal end 124, and distal plate 140 extends between top and bottom pieces 122, 128 and toward proximal plate 134. The distal plate is movable to a second position (FIG. 39) in which distal plate free edge 144 is engaged in bottom piece groove 146. In the second position, distal plate 140 is generally parallel to proximal plate 134.

Figure 44:
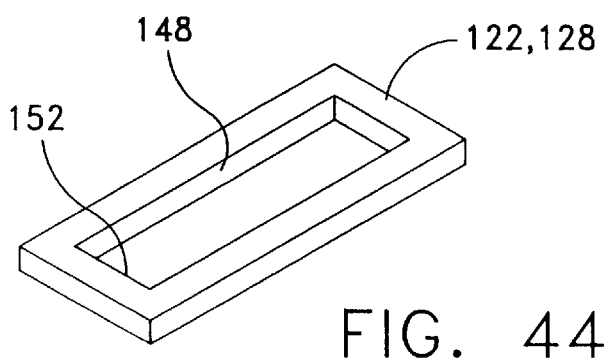
FIG. 44 is a diagrammatic illustration of an alternative configuration of top piece and/or bottom piece of the spacer.

Referring again to FIGS. 35, 37 and 39, it will be seen that top and bottom pieces 122 and 128, comprise, respectively, top and bottom plates which are provided with openings 148 therein which may be a series of holes 150. In FIG. 44 there is shown an alternative embodiment of top and/or bottom pieces 122 and 128, wherein the top and bottom pieces comprise, respectively, top and bottom frame members and the openings 148 are slots 152 defined by the frame members. The openings 148 will be further discussed hereinbelow.

Figure 40:
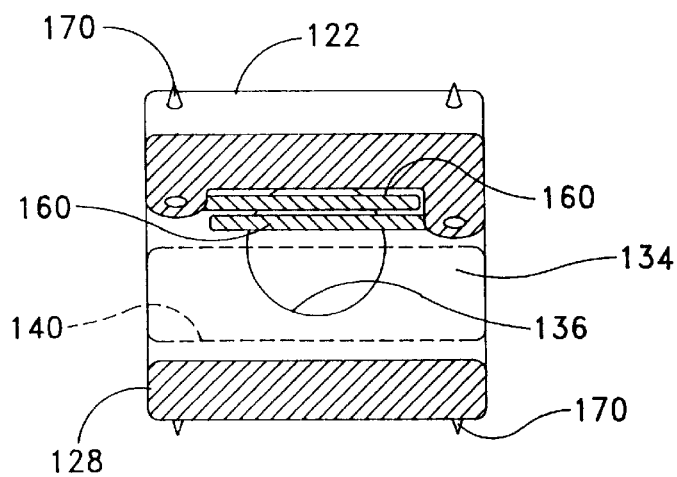
FIG. 40 is a sectional view taken along line 40-40 of FIG. 35.
Figure 41:
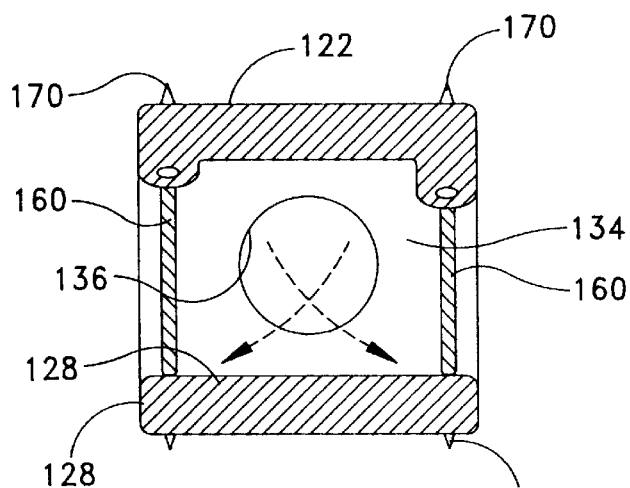
FIG. 41 is a sectional view taken along 41-41 of FIG. 39.

If desired, spacer 120 may also be provided with side plates 160 (FIG. 40) which are hingedly mounted on opposite sided edges of top piece 122 and are biased by spring means (not shown), which may be leaf springs or wire springs, to move side plates 160 from the position shown in FIG. 40 (wherein side plates 160 are substantially parallel to top piece 122) to the position shown in FIG. 41, wherein side plates 160 are substantially normal to top and bottom pieces 122, 128. In the contracted state of the spacer, shown in FIG. 35, the distal plate 140 extends between the top and bottom pieces 122, 128 and prevents side walls 160 from springing outwardly. However, when the spacer is expanded, as shown in FIG. 39, distal plate 140 is removed from a side plate blocking position and the spring-biased side plates 160 can spring outwardly to engage bottom piece 128 and substantially close off the side spaces between the top and bottom pieces 122, 128. If desired, side plates 160 may be provided with a plurality of tiny holes (not shown) to permit blood to flow into and out of the region defined by the expanded spacer 120 (FIG. 41).

As shown in FIGS. 35–41, top and bottom pieces 122, 128, may be provided with pins 170 upstanding from top piece 122 and depending from bottom piece 128. The pins 170 are adapted to engage the neighboring vertebrae Va, Vb.

The spacer 120 is made of a substantially rigid material of sufficient strength to maintain support between vertebrae Va, Vb. Preferably, the material of spacer 120 is bio-absorbable, further discussed hereinbelow.

An inserter tool 180 is provided for insertion of the spacer 120 into a space between vertebrae Va, Vb. The inserter tool 180 includes an outer tubular member 182 releaseably connectable to proximal plate 134 so as to be disposed around proximal plate central hole 136. The connection means for connecting outer tubular member 182 to proximal plate 134 preferably is the same as the connection means 66 shown in FIGS. 11, 13, and 16.

Inserter tool 180 further includes a rod 184 movable axially in tubular member 182 and through proximal plate central hole 136. Rod 184 is provided with a distal end 186 which is engageable with distal plate 140 to move the distal plate from the position shown in FIG. 35 to the position shown in FIG. 39, that is, from the contracted condition to the expanded condition.

Figure 43:
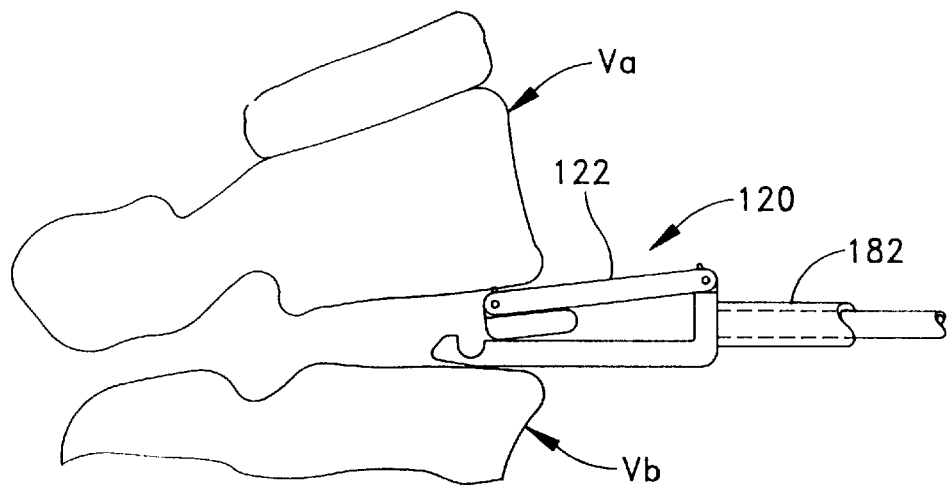
FIG. 43 is a diagrammatic illustration showing the manner of inserting the spacer in a spinal column.

In use, the above-described spacer 120 is provided in the condition shown in FIG. 35, wherein the spacer is of a generally wedge-shaped configuration. The tubular member 182 is connected to proximal plate 134 by connecting means 66. As shown diagrammatically in FIG. 43, the wedge-shaped spacer 120 is inserted into the gap between vertebrae Va, Vb and is driven into the gap by force exerted on tubular member 182. In use of this embodiment, a jack is typically not required. As noted above, a jack is often used to spread vertebra Va, Vb apart to permit insertion of a spacer. However, in use of the present embodiment, the wedge-shaped spacer 120 may be driven into the space between vertebrae Va, Vb.

The rod 184 is then introduced into tubular member 182 and moved axially therethrough and through proximal plate hole 136, and through spacer 120, until rod distal end 186 engages distal plate 140. Continued distal movement of rod 184 pivots distal plate 140 (FIGS. 37 and 38) from a substantially horizontal position, as shown in FIGS. 35 and 36, to a substantially vertical position, as shown in FIG. 39. The free edge 144 of distal plate 140 snaps into bottom piece groove 146 to lock spacer 120 in the expanded condition. Movement of distal plate 140 to the position shown in FIG. 39 frees side plates 160 which are spring-biased to move into the side closure positions shown in FIG. 41. The rod 184 may then be withdrawn from the spacer 120 and tubular member 182, and the tubular member 182 disconnected from proximal plate 134 and withdrawn from the operative site, leaving spacer 120 in place. Typically, the insertion of two such spacers is required, the spacers being positioned essentially side by side.

Preferably, the outer tubular member 182 and, in some instances, rod 184 are used to inject a selected material 106 into spacer 120 before inserter tool 180 is removed from the surgical site. When rod 184 is of a tubular structure, the material 106 may be flowed from a material source, through rod 184, and into spacer 120. When rod 184 is of a solid construction, rod 184 may be removed and the material flowed through tube 182. Alternatively, a separate tube (not shown) may be substituted for rod 184 and used for injection of the filler material. The filler material is of the type described above with respect to foregoing embodiments of spacers, and is often of the type encouraging fusion of vertebrae Va, Vb.

To that end, the openings 148 permit flow of the material upwardly and downwardly from spacer 120 to come into contact with adjacent surfaces of vertebrae Va, Vb. If the spacer is of bio-absorbable material, as may be preferred, the vertebrae, over time, gradually fuse to one another while the spacer gradually disappears, leaving the vertebrae fused together with no intermediary spacer.

Figure 42:
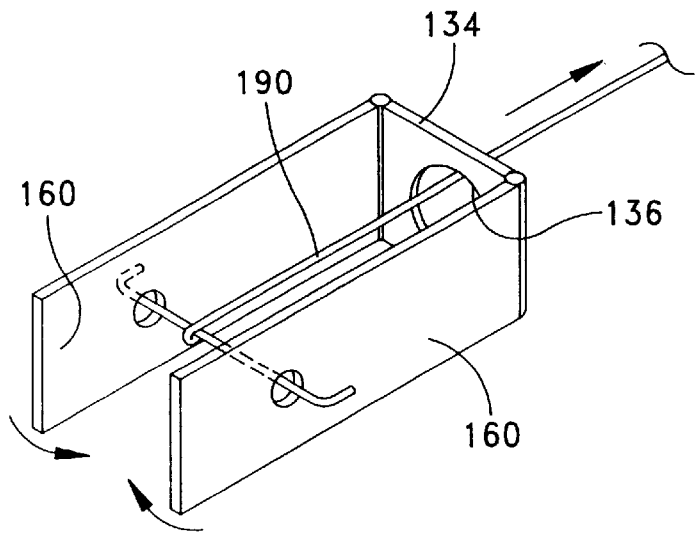
FIG. 42 is a diagrammatic illustration of means employed in collapsing the spacer for removal from an operative site.

In the event that it is necessary to remove spacer 120, a hook-like snagger 190 (FIG. 42) may be passed through proximal plate hole 136 to snag a wire 192, and pulled proximally to pull side plates 160 toward one another. Another snagger (not shown) of the same type as snagger 190 may then be passed through proximal plate hole 136 to snag a loop (not shown) on the inside surface of distal plate 140, and pulled upwardly and proximally to pull the free edge 144 of distal plate 140 from groove 146 and move distal plate 140 toward the position shown in FIG. 35, whereupon spacer 120, in the contracted state, may be withdrawn from the spinal column.

In the present invention, material 106 may comprise fusion-enhancing materials, therapeutic agents, artificial disc components, and the like. Furthermore, fluid material 106 may be of the type wherein it is inserted into the surgical site in one condition (e.g., a low viscosity fluid state so as to be able to flow easily) and then transformed in situ (e.g., by the application of heat or light or by a chemical reaction, etc.) into a second condition (e.g., a high viscosity fluid state so as to remain in place). Further, the fluid material 106 may be any one of a liquid, a paste, a gel, and a substantially dry particulate.

In the foregoing discussions of the various spacers of the present invention, the spacers were discussed in the context of opening distally, away from the user. It should be appreciated, however, that it is also possible to construct and use the spacers of the present invention so that that they will open proximally, toward the user.

Thus, for example, FIGS. 45 and 46 show a spacer 40A which is arranged so as to open proximally toward the user. Spacer 40A is substantially the same as the spacer 40 described above, except that the various wall elements 52A, 54A, 62A and 64A have the slightly different geometry shown so as to facilitate proximal opening of the spacer. Spacer 40A is deployed by advancing the collapsed spacer to the surgical site so that its distal connector wall element 52A resides in the desired location, and then holding the inserter tool's first portion 92A steady while pulling proximally on the inserter tool's second portion 96A so as to expand spacer 40A proximally toward the user, so as to achieve the expanded state shown in FIG. 46.

Corresponding arrangements and methods of use can be utilized for each of the various other spacers described above.

It will be appreciated that proximal opening of the spacers may be desirable in situations where critical anatomical structures may lie on the far side of the spacer, such that distal opening of the spacer might bring the expanded spacer closer to the structure which is to be avoided.

There is thus provided a spacer for insertion between adjacent vertebrae. The spacer is collapsible to a first relatively small configuration for passage through an incision, and expandable to a second relatively large configuration to replace a natural intervertebral disc. There is further provided an inserter tool assembly. There is still further provided a method for emplacing an intervertebral spacer, wherein the approach to spacer emplacement may be undertaken through the abdominal cavity. In one preferred embodiment of the invention, the spacer is positioned in the patient's spine using an abdominal approach. It is also to be appreciated that the spacer can be positioned in the patient's spine using either a laparoscopic abdominal (anterior) approach or an "open incision" abdominal approach, with the path of entry being either head-on or oblique. Furthermore, it should be appreciated that the spacer can also be positioned in the patient's spine using a posterior (i.e., rear) approach. Again, such an approach can be via either a laparoscopic or "open incision" technique, and the path of entry can be either straight or oblique. Thus, the spacer can be positioned in the patient's spine from essentially any direction, limited only by anatomical considerations.

It is to be understood that the present invention is by no means limited to the particular constructions and method steps herein disclosed and/or shown in the drawings, but also comprises any modifications or equivalents within the scope of the claims. For example, it will be apparent to those skilled in the art that while wall elements of straight configuration hold advantages in manufacture and assembly, elements of any desired configuration can be used, including curved elements.

What is claimed is:

1. An intervertebral spacer comprising a plurality of discrete wall elements connected in series to form a body; said discrete wall elements being collapsible to a first non-expanded configuration, said first non-expanded configuration including at least some of said discrete wall elements being disposed internally of others of said discrete wall elements; and expandable to a second configuration, said second configuration including said discrete wall elements forming said body to define an outer expanded periphery of said body.

2. An intervertebral spacer according to claim 1 wherein each of said discrete wall elements is an elongated rigid member.

3. An intervertebral spacer according to claim 2 wherein said elongated member comprises a straight portion intermediate a pair of ends, and said elongated member is pivotally connected to adjacent elongated members at each end thereof.

4. An intervertebral spacer according to claim 3 wherein said elongated members are pivotally connected by a hinge.

5. An intervertebral spacer according to claim 3 wherein said hinge construction comprises pivot pins.

6. An intervertebral spacer according to claim 5 wherein extensions of at least some of said pivot pins extend beyond said spacer to engage at least one vertebra adjacent to said spacer.

7. An intervertebral spacer according to claim 1 wherein said discrete wall elements include a discrete distal connector wall element pivotally connected at each end thereof to an adjoining one of said discrete wall elements, said discrete distal connector wall element being adapted for connection to a first portion of an inserter tool, said discrete distal connector wall element and said adjoining ones of said discrete wall elements comprising at least a portion of said discrete wall elements disposed internally of other of said discrete wall elements when said discrete wall elements are disposed in said first non-expanded configuration, said discrete distal connector wall element and said adjoining ones of said discrete wall elements being movable by said first portion of said inserter tool to said outer expanded periphery of said body when said discrete wall elements are disposed in said second configuration.

8. An intervertebral spacer according to claim 7 wherein said wall elements include a discrete proximal connector wall element pivotally connected at each end thereof to an adjacent one of said discrete wall elements, said discrete proximal connector wall element being adapted for connection to a second portion of said inserter tool, said discrete proximal connector wall element and said adjacent ones of said discrete wall elements comprising at least a portion of said other of said discrete wall elements.

9. An intervertebral spacer according to claim 8 wherein said elongated member comprises a portion intermediate a pair of ends, and said elongated member is pivotally connected to adjacent elongated members at each end thereof.

10. An intervertebral spacer according to claim 1 wherein a portion of said wall elements each comprises a body of elastomeric material, and wherein said wall elements are connected to one another by a living hinge.

11. A method for emplacement of an intervertebral spacer comprising the steps of:

providing an intervertebral spacer comprising a plurality of discrete wall elements connected in series to form a body; said discrete wall elements being collapsible to a first non-expanded configuration, said first non-expanded configuration including at least some of said discrete wall elements being disposed internally of others of said discrete wall elements; and expandable to a second configuration, said second configuration including said discrete wall elements forming said body to define an outer expanded periphery of said body;

inserting said spacer in said first non-expanded configuration between two vertebrae; and expanding said spacer to said second configuration.

12. A method in accordance with claim 11 comprising the further step of filling an inner cavity as defined by said discrete wall elements.

13. A method according to claim 12 wherein said fluid material is a material selected from a group of materials consisting of liquids, pastes, gels, and substantially dry particulates.

14. A method for emplacement of an intervertebral spacer comprising the steps of:

providing an intervertebral spacer comprising a plurality of discrete wall elements connected in series to form a body; said discrete wall elements being collapsible to a first non-expanded configuration, said first non-expanded configuration including at least some of said discrete wall elements being disposed internally of others of said wall elements; and expandable to a second configuration, said second configuration including said discrete wall elements forming said body to define an outer expanded periphery of said body, said discrete wall elements including a discrete proximal connector wall element and a discrete distal connector wall element;

providing a tool having a first portion thereof for connection to said discrete distal connector wall element, and a second portion thereof for connection to said discrete proximal connector wall element, said first portion being movable axially in said second portion;

connecting said tool second portion to said discrete proximal connector wall element and connecting said tool first portion to said discrete distal connector wall element, and positioning said spacer in said first non-expanded configuration;

extending said tool second portion, with said tool first portion therein, through a patient's body toward a space between two adjacent vertebrae, with said spacer in said first non-expanded configuration;

placing said spacer, while in said first non-expanded configuration, in said space;

manipulating said tool so as to move said spacer from said first non-expanded configuration to said second configuration;

disconnecting said tool first portion from said spacer and withdrawing said tool first portion from said spacer; and disconnecting said tool second portion from said spacer and withdrawing said tool from said spacer and from the patient's body.

15. A method according to claim 14 comprising the further step of filling an inner cavity as defined by said discrete wall elements.

16. A method according to claim 14 wherein said spacer is advanced into the patient's body through the abdominal cavity.

17. A method according to claim 14 wherein said spacer is advanced into the patient's body using a posterior approach.

18. A method according to claim 14 wherein said spacer is advanced laterally into the patient's body from one side of the patient's body.

19. An intervertebral spacer according to claim 1 wherein said discrete wall elements include a discrete distal connector wall element pivotally connected at each end thereof to an adjacent one of said discrete wall elements, said discrete distal connector wall element being adapted for connection to a first portion of an inserter tool, and further wherein said discrete wall elements include a discrete proximal connector wall element pivotally connected at each end thereof to an adjoining one of said discrete wall elements, said discrete proximal connector wall element being adapted for connection to a second portion of said inserter tool, said discrete proximal connector wall element and said adjoining ones of said discrete wall elements comprising at least a portion of said discrete wall elements disposed internally of others of said discrete wall elements when said discrete wall elements are disposed in said first non-expanded configuration, said discrete proximal connector wall element and said adjoining ones of said discrete wall elements being movable by said second portion of said inserter tool to said outer expanded periphery of said body when said discrete wall elements are disposed in said second configuration.

20. An intervertebral spacer according to claim 19 wherein said discrete distal connector wall element and said adjacent ones of said discrete wall elements comprise at least a portion of said other of said discrete wall elements.

\* \* \* \* \*